(12) United States Patent
Wang et al.

(10) Patent No.: US 8,999,245 B2
(45) Date of Patent: Apr. 7, 2015

(54) CASCADED GAS CHROMATOGRAPHS (CGCS) WITH INDIVIDUAL TEMPERATURE CONTROL AND GAS ANALYSIS SYSTEMS USING SAME

(75) Inventors: Li-Peng Wang, San Jose, CA (US); Chien-Lin Huang, Sinjhuang (TW); Tsung-Kuan A. Chou, San Jose, CA (US)

(73) Assignee: Tricorn Tech Corporation, San Jose, CA (US)

( * ) Notice: Subject to any disclaimer, the term of this patent is extended or adjusted under 35 U.S.C. 154(b) by 235 days.

(21) Appl. No.: 12/830,682

(22) Filed: Jul. 6, 2010

(65) Prior Publication Data

US 2011/0005300 A1    Jan. 13, 2011

Related U.S. Application Data

(60) Provisional application No. 61/223,678, filed on Jul. 7, 2009.

(51) Int. Cl.
| | |
|---|---|
| *B01D 53/02* | (2006.01) |
| *G01N 30/46* | (2006.01) |
| *G01N 30/30* | (2006.01) |
| *G01N 30/60* | (2006.01) |
| *G01N 30/88* | (2006.01) |

(52) U.S. Cl.
CPC .............. *G01N 30/461* (2013.01); *G01N 30/30* (2013.01); *G01N 30/463* (2013.01); *G01N 30/6095* (2013.01); *G01N 2030/8881* (2013.01)

(58) Field of Classification Search
USPC .............................. 73/23.4, 23.35; 422/70, 89
See application file for complete search history.

(56) References Cited

U.S. PATENT DOCUMENTS

| | | | | |
|---|---|---|---|---|
| 3,538,744 | A | * | 11/1970 | Karasek ........................ 73/23.39 |
| 4,470,298 | A | | 9/1984 | Jibelian |
| 4,869,876 | A | * | 9/1989 | Arfman et al. ................... 422/89 |
| 4,873,058 | A | * | 10/1989 | Arnold et al. ................... 422/89 |
| 4,888,295 | A | | 12/1989 | Zaromb et al. |
| 5,092,155 | A | | 3/1992 | Rounbehler et al. |
| 5,108,468 | A | | 4/1992 | Ligon, Jr. |
| 5,108,705 | A | | 4/1992 | Rounbehler et al. |
| 5,109,691 | A | | 5/1992 | Corrigan et al. |

(Continued)

FOREIGN PATENT DOCUMENTS

| | | |
|---|---|---|
| CN | 2192933 | 3/1995 |
| CN | 2439025 | 7/2001 |

(Continued)

OTHER PUBLICATIONS

PCT/US2011/033325, International Search Report and Written Opinion of the International Searching Authority, mail date Jan. 6, 2012, 7 pages.

(Continued)

*Primary Examiner* — David A Rogers
(74) *Attorney, Agent, or Firm* — Blakely Sokoloff Taylor & Zafman LLP

(57) ABSTRACT

The disclosure describes a cascaded gas chromatograph including a first gas chromatograph having a first temperature control and a second gas chromatograph coupled to the first gas chromatograph. The first and second chromatographs have individual temperature controls that can be controlled independently of each other. Other embodiments are disclosed and claimed.

8 Claims, 19 Drawing Sheets

(56) References Cited

U.S. PATENT DOCUMENTS

| | | | |
|---|---|---|---|
| 5,376,252 A * | 12/1994 | Ekstrom et al. | 204/603 |
| 5,471,055 A | 11/1995 | Costanzo et al. | |
| 5,611,846 A | 3/1997 | Overton et al. | |
| 5,770,088 A * | 6/1998 | Ikeda et al. | 210/659 |
| 6,258,263 B1 * | 7/2001 | Henderson et al. | 210/198.2 |
| 6,306,200 B1 * | 10/2001 | Yu | 96/102 |
| 6,497,138 B1 | 12/2002 | Abdel-Rahman et al. | |
| 6,759,013 B2 * | 7/2004 | Kaltenbach et al. | 422/504 |
| 6,828,910 B2 | 12/2004 | VanRyzin et al. | |
| 6,914,220 B2 | 7/2005 | Tian et al. | |
| 7,153,272 B2 | 12/2006 | Talton | |
| 7,273,517 B1 * | 9/2007 | Lewis et al. | 96/101 |
| 7,343,779 B1 | 3/2008 | Yu | |
| 7,437,779 B2 | 10/2008 | Kenny et al. | |
| 7,530,259 B2 * | 5/2009 | Tai et al. | 73/61.57 |
| 7,608,818 B2 * | 10/2009 | Miller et al. | 250/288 |
| 7,926,368 B2 | 4/2011 | Ryan | |
| 8,087,283 B2 | 1/2012 | Wang et al. | |
| 8,277,544 B2 * | 10/2012 | Guan et al. | 96/101 |
| 2003/0015019 A1 | 1/2003 | O'Brien | |
| 2003/0233862 A1 * | 12/2003 | Wise et al. | 73/23.39 |
| 2004/0236244 A1 | 11/2004 | Allen et al. | |
| 2005/0063865 A1 | 3/2005 | Bonne et al. | |
| 2005/0065446 A1 | 3/2005 | Talton | |
| 2005/0085740 A1 | 4/2005 | Davis et al. | |
| 2005/0223775 A1 * | 10/2005 | Klee et al. | 73/23.41 |
| 2005/0264926 A1 | 12/2005 | Burts-Cooper et al. | |
| 2005/0274174 A1 * | 12/2005 | Tai et al. | 73/61.57 |
| 2006/0046749 A1 | 3/2006 | Pomerantz et al. | |
| 2006/0222568 A1 | 10/2006 | Wang et al. | |
| 2007/0000305 A1 | 1/2007 | Ma et al. | |
| 2007/0000838 A1 | 1/2007 | Shih et al. | |
| 2007/0029477 A1 * | 2/2007 | Miller et al. | 250/290 |
| 2007/0062255 A1 | 3/2007 | Talton | |
| 2007/0256474 A1 | 11/2007 | Paakkanen et al. | |
| 2008/0092626 A1 | 4/2008 | Lehmann | |
| 2008/0121016 A1 * | 5/2008 | Shah et al. | 73/23.42 |
| 2008/0233636 A1 | 9/2008 | Ryan | |
| 2008/0264491 A1 | 10/2008 | Klee et al. | |
| 2008/0300501 A1 | 12/2008 | Willard et al. | |
| 2009/0238722 A1 * | 9/2009 | Mora-Fillat et al. | 422/68.1 |
| 2009/0308136 A1 | 12/2009 | Wang et al. | |
| 2009/0321356 A1 * | 12/2009 | Gerhardt et al. | 210/656 |
| 2011/0023581 A1 | 2/2011 | Chou et al. | |
| 2011/0113866 A1 * | 5/2011 | Finlay | 73/61.52 |
| 2011/0143952 A1 * | 6/2011 | Lewis et al. | 506/8 |
| 2011/0259081 A1 | 10/2011 | Chou et al. | |
| 2012/0090378 A1 | 4/2012 | Wang et al. | 73/23.42 |

FOREIGN PATENT DOCUMENTS

| | | |
|---|---|---|
| CN | 2520508 | 11/2002 |
| CN | 1584589 A | 2/2005 |
| CN | 2798088 | 7/2006 |
| CN | 2859526 | 1/2007 |
| CN | 1954208 A | 4/2007 |
| CN | 1979172 A | 6/2007 |
| CN | 101196457 A | 6/2008 |
| CN | 201133905 Y | 10/2008 |
| DE | 196 01 571 A1 | 7/1997 |
| EP | 0 573 060 A2 | 12/1993 |
| EP | 0 574 027 A2 | 12/1993 |
| EP | 0 654 667 A1 | 5/1995 |
| EP | 2 065 704 A1 | 6/2009 |
| GB | 874 742 | 8/1961 |
| JP | 06 242095 A | 9/1994 |
| JP | 07 318545 A | 12/1995 |
| JP | 2009-183905 | 8/2009 |
| WO | WO 2009/057256 A1 | 5/2009 |

OTHER PUBLICATIONS

Manolis, A., "The Diagnostic Potential of Breath Analysis," Clinical Chemistry, vol. 29, No. 1, pp. 5-15, (1983).

Ho, C. K. et al., "Review of Chemical Sensors for In-Situ Monitoring of Volatile Contaminants," Sandia Report, SAND2001-0643, pp. 1-28, (2001).

Riegel, J. et al., "Exhaust gas sensors for automotive emission control," Elsevier, Solid State Ionics 152-153, pp. 783-800, (2002).

Eranna, G. et al., "Oxide Materials for Development of Integrated Gas Sensors—A Comprehensive Review," Critical Reviews in Solid State and Materials Sciences, 29, pp. 111-188, (2004).

Arshak, K. et al., "A review of gas sensors employed in electronic nose applications," Sensor Review, vol. 24, No. 2, pp. 181-198, (2004).

Yamazoe, N., "Toward innovations of gas sensor technology," Elsevier, Sensors and Actuators B 108, pp. 2-14, (2005).

Cao, W. et al., "Breath Analysis: Potential for Clinical Diagnosis and Exposure Assessment," Clinical Chemistry 52, No. 5, pp. 800-811, (2006).

Buszewski, B. et al., "Human exhaled air analytics: biomarkers of diseases" Review, Biomedical Chromatography, 21, pp. 553-566, (2007).

Ohira, S.-I. et al., "Micro gas analyzers for environmental and medical applications," Elsevier, Science Direct, Analytica Chimica Acta 619, pp. 143-156, (2008).

Peng, G. et al., "Diagnosing lung cancer in exhaled breath using gold nanoparticles," Nature Nanotechnology, vol. 4, pp. 669-673, (2009).

Barnes, P. J. et al., "Exhaled Nitric Oxide in Pulmonary Diseases: A Comprehensive Review," Chest, Official publication of the American College of Chest Physicians, 138/3, pp. 682-692, (2010).

Rollins, G., "Beyond Breathalyzers: What Clinical Niche Will Breath Tests Fill?" Clinical Laboratory News, vol. 37, No. 5, pp. 1-6, (2011).

Wohltjen, H. et al., "Colloidal Metal-Insulator-Metal Ensemble Chemiresistor Sensor," Analytical Chemistry, vol. 70, No. 14, Jul. 15, 1998, pp. 2856-2859.

Tian, W. et al., "Multiple-Stage Microfabricated Preconcentrator-Focuser for Micro Gas Chromatography System," Journal of Microelectromechanical Systems, vol. 14, No. 3, Jun. 2005, pp. 498-507.

PCT/US2010/041243, International Search Report and Written Opinion of the International Searching Authority, mail date Feb. 17, 2011, 7 pages.

de Alencastro, L. F. et al., "Application of Multidimensional (Heart-Cut) Gas Chromatography to the Analysis of Complex Mixtures of Organic Pollutants in Environmental Samples," Environmental Analysis, Chimia 57, No. 9, (2003) pp. 499-504.

Lambertus, G. et al., "Stop-Flow Programmable Selectivity with a Dual-Column Ensemble of Microfabricated Etched Silicon Columns and Air as Carrier Gas," Analytical Chemistry, vol. 77, No. 7, Apr. 1, 2005, pp. 2078-2084.

Phillips, M. et al., "Breath biomarkers of active pulmonary tuberculosis," Elsevier, Diagnostics, Tuberculosis (2010) pp. 1-7.

PCT/US2009/045872, International Search Report and Written Opinion of the International Searching Authority, mail date Jul. 27, 2009, 11 pages.

PCT/US2010/044165, International Search Report and Written Opinion of the International Searching Authority, mail date Apr. 29, 2011, 8 pages.

U.S. Office Action mailed Dec. 22, 2010, U.S. Appl. No. 12/140,822, filed Jun. 17, 2008, 16 pages.

U.S. Office Action mailed May 18, 2011, U.S. Appl. No. 12/140,822, filed Jun. 17, 2008, 6 pages.

U.S. Notice of Allowance mailed Aug. 30, 2011, U.S. Appl. No. 12/140,822, filed Jun. 17, 2008, 9 pages.

Libardoni, M. et al., "Analysis of human breath samples with a multi-bed sorption trap and comprehensive two-dimensional gas chromatography (GC×GC)," Elsevier, Science Direct, Journal of Chromatography B, 842, (2006), pp. 13-21.

R. Dutta et al., "Bacteria classification using Cyranose 320 electronic nose," BioMedical Engineering OnLine 2002, Published: Oct. 16, 2002, pp. 1-7.

G. Lambertus et al., "Design, Fabrication, and Evaluation of Microfabricated Columns for Gas Chromatography," Analytical Chemistry, vol. 76, No. 9, May 1, 2004, pp. 2629-2637.

C.W. Hanson III, M.D. et al., "Electronic Nose Prediction of a Clinical Pneumonia Score: Biosensors and Microbes," Anesthesiology, V 102, No. 1, Jan. 2005, pp. 63-68.

(56) References Cited

OTHER PUBLICATIONS

M. Phillips et al., "Volatile biomarkers of pulmonary tuberculosis in the breath," Tuberculosis (2007) 87, pp. 44-52.
B. Bae et al., "A Fully-Integrated MEMS Preconcentrator for Rapid Gas Sampling," Transducers & Eurosensors'07, The 14th International Conference on Solid-State Sensors, Actuators and Microsystems, Lyon, France, Jun. 10-14, 2007, 2007 IEEE, pp. 1497-1500.
M. Phillips et al., "Prediction of lung cancer using volatile biomarkers in breath[1]," IOS Press, Cancer Biomarkers 3, (2007), pp. 95-109.
M.P. Rowe et al., "Exploiting Charge-Transfer Complexation for Selective Measurement of Gas-Phase Olefins with Nanoparticle-Coated Chemiresistors," Analytical Chemistry, vol. 79, No. 3, Feb. 1, 2007, pp. 1164-1172.
EP Application No. 09767436.0, Supplementary European Search Report and the European Search Opinion, Dec. 22, 2011, 8 pages.
U.S. Appl. No. 13/332,064—Non-Final Office Action, mailed Nov. 5, 2012, 24 pages.
U.S. Appl. No. 12/847,593—Non-Final Office Action, mailed Dec. 20, 2012, 6 pages.
Tian, W. et al., "Microfabricated Preconcentrator-Focuser for a Microscale Gas Chromatograph," Journal of Microelectromechanical Systems, vol. 12, No. 3, Jun. 2003, pp. 264-272.
A. Hansel et al., "Proton transfer reaction mass spectrometry: on-line trace gas analysis at the ppb level," International Journal of Mass Spectrometry and Ion Processes, vols. 149-150, Nov. 15, 1995, pp. 609-619.
Auble, D.L. et al., "An open path, fast response infrared absorption gas analyzer for H2O and CO2," Boundary-Layer Meteorology, 1992, vol. 59, pp. 243-256.
Y. Aimin et al., "Analysis of Gas by a Portable Gas Chromatograph With a Microwave Induced Plasma Ionization Detector," Chinese Journal of Analytical Chemistry, 1993, vol. 21, No. 6, pp. 736-739.
Y. Haiying et al., "A New GC System for the Analysis of Permanent Gases," Rock and Mineral Analysis, Mar. 1999, vol. 18, No. 1, pp. 29-33, Beijing, China.
B. Shi, "Application of 4 200 Ultra-fast GC Analyzer to Environment Emergence Monitoring," Liaoning Urban and Rural Environmental Science & Technology, 2006, vol. 26, No. 6, pp. 34-35.
CN 2010-80031094.9—First Chinese Office Action, mailed Sep. 12, 2013, 15 pages.
U.S. Appl. No. 12/847,593—Final Office Action, mailed Jul. 18, 2013, 8 pages.
U.S. Appl. No. 13/332,064—Non-Final Office Action, mailed Jun. 7, 2013, 23 pages.
CN 2009-80123127.X—Second Chinese Office Action, mailed Sep. 24, 2013, 13 pages.
EP 10 79 7800—EPO Communication pursuant to Article 153(7) EPC, dated Sep. 25, 2013, 6 pages.
JP 2011-514674—First Japanese Office Action, mailed Nov. 12, 2013, 8 pages.
CN 2010-80040138.4—First Chinese Office Action, mailed Oct. 28, 2013, 14 pages.
U.S. Appl. No. 12/847,593—Notice of Allowance, mailed Nov. 19, 2013, 11 pages.
U.S. Appl. No. 13/332,064—Notice of Allowance, mailed Nov. 25, 2013, 12 pages.
Abstract of Liu Juntao et al., "Multi-Dimensional Gas Chromatography for Analysis of Refinery Gas," Modern Instruments, vol. 6, pp. 48-51.
CN 2010-80040138.4—Notice of Allowance, mailed Feb. 20, 2014, 13 pages.
CN 2009-80123127.X—First Chinese Office Action, issued Feb. 1, 2013, 27 pages.
CN 2011-80026437.7—First Chinese Office Action, issued Jan. 6, 2014, 20 pages.
CN 2009-80123127.X—Second Chinese Office Action, issued Apr. 21, 2014, 12 pages.
CN 2011-514674—Notice of Allowance, issued Jun. 19, 2014, 3 pages.

\* cited by examiner

US 8,999,245 B2

CASCADED GAS CHROMATOGRAPHS (CGCS) WITH INDIVIDUAL TEMPERATURE CONTROL AND GAS ANALYSIS SYSTEMS USING SAME

CROSS-REFERENCE TO RELATED APPLICATIONS

This application claims priority under 35 U.S.C. §119(e) to U.S. Provisional Patent Application No. 61/223,678, filed 7 Jul. 2009.

TECHNICAL FIELD

The present invention relates generally to cascaded gas chromatograph (CGCs) and in particular, but not exclusively, to CGCs including gas chromatographs with individual temperature control and to gas analysis systems using such CGCs.

BACKGROUND

Gas analysis can be an important means for detecting the presence and concentration of certain chemicals in the gas and determining the meaning of the particular combination of chemicals present. In health care, for example, the presence of certain volatile organic compounds (VOCs) in exhaled human breath are correlated to certain diseases, such as pneumonia, pulmonary tuberculosis (TB), asthma, lung cancer, liver diseases, kidney diseases, etc. The correlations are especially evidential for lung-related diseases. In other applications, gas analysis can be used to determine the presence of dangerous substances incompatible with human presence, such as methane, carbon monoxide or carbon dioxide in a mine.

Current gas analytical systems still rely heavily on large and expensive laboratory instruments, such as gas chromatography (GC) and mass spectrometry (MS). Most of these instruments (mass spectrometers in particular) have operational characteristics that prevent significant reductions in their size, meaning that current gas analysis systems are large and expensive bench devices. In addition to being expensive and unwieldy, the large size of current gas analysis devices makes widespread use of these instruments impossible.

GC column coatings are usually optimized for specific temperatures and chemicals, so that no single GC can separate a large array of chemicals, even by varying its temperature. Because existing GCs are large, heavy units housed in labs, a carrier gas with many chemicals may need to be sent to multiple locations for separation, which substantially increases cost.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION OF THE ILLUSTRATED EMBODIMENTS

Embodiments of an apparatus, process and system for gas analysis in point-of-care medical applications are described herein. In the following description, numerous specific details are described to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail but are nonetheless encompassed within the scope of the invention.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in this specification do not necessarily all refer to the same embodiment. Furthermore, the particular features, structures, or characteristics may be combined in any suitable manner in one or more embodiments.

Figure 1A:
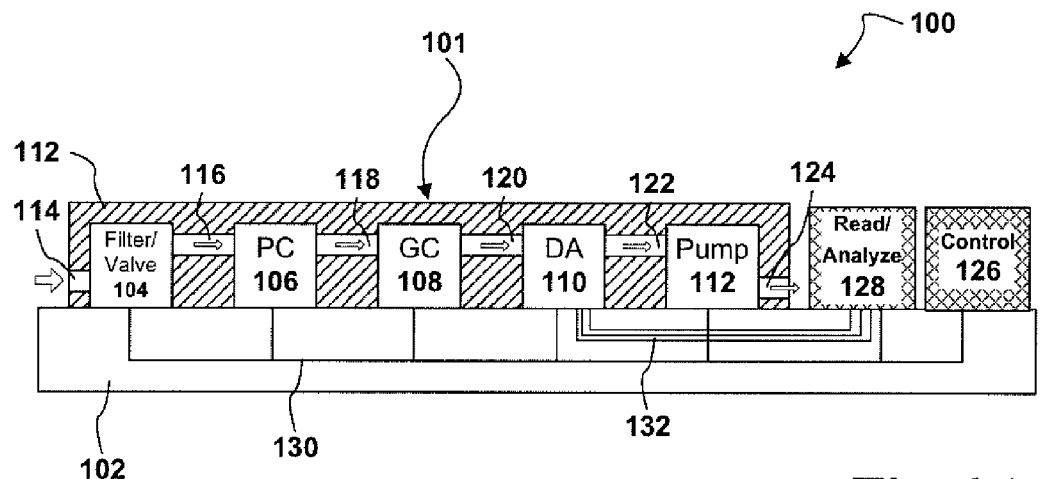
FIG. 1A is a side elevation drawing of an embodiment of a gas analysis device.
Figure 1B:
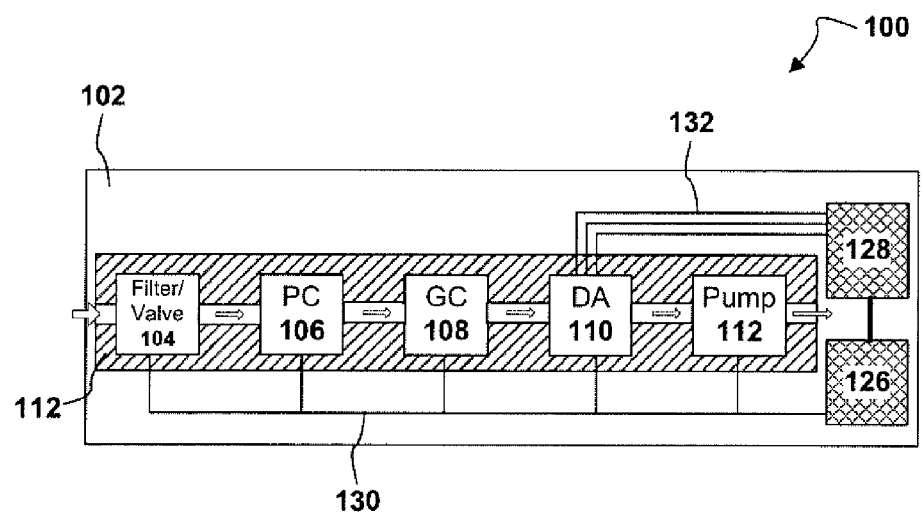
FIG. 1B is a plan view of the embodiment of a gas analysis device shown in FIG. 1.

FIGS. 1A and 1B together illustrate an embodiment of a small scale (e.g., handheld) gas analysis device 100. Device 100 includes a substrate 102 on which are mounted a fluid handling assembly 101, a controller 126 coupled to the individual elements within fluid handling assembly 101, and a reading and analysis circuit 128 coupled to detector array 110 and to controller 126. The embodiment shown in the figures illustrates one possible arrangement of the elements on substrate 102, but in other embodiments the elements can, of course, be arranged on the substrate differently.

Substrate 102 can be any kind of substrate that provides the required physical support and communication connections for the elements of device 100. In one embodiment, substrate 102 can be a printed circuit board (PCB) of the single-layer variety with conductive traces on its surface, but in other embodiments it can be a PCB of the multi-layer variety with conductive traces in the interior of the circuit board. In other embodiments, for example an embodiment where device 100 is built as a monolithic system on a single die, substrate 102 can be chip or wafer made of silicon or some other semiconductor. In still other embodiments, substrate 102 can also be a chip or wafer in which optical waveguides can be formed to support optical communication between the components of device 100.

Fluid handling assembly 101 includes a filter and valve assembly 104, a pre-concentrator 106, a gas chromatograph 108, a detector array 110 and a pump 112. Elements 104-112 are fluidly coupled in series: filter and valve assembly 104 is fluidly coupled to pre-concentrator 106 by fluid connection 116, pre-concentrator 106 is fluidly coupled to gas chromatograph 108 by fluid connection 118, gas chromatograph 108 is fluidly coupled to detector array 110 by fluid connection 120, and detector array 110 is coupled to pump 112 by fluid connection 122. As further described below, in one embodiment of device 100 elements 104-112 can be micro-electro-mechanical (MEMS) elements or MEMS-based elements, meaning that some parts of each device can be MEMS and other parts not. In other embodiments of device 100, some or all of elements 104-112 need not be MEMS or MEMS-based, but can instead be some non-MEMS chip scale device.

As indicated by the arrows in the figures, the fluid connections between elements 104-112 allow a fluid (e.g., one or more gases) to enter filter and valve assembly 104 through inlet 114, flow though elements 104-112, and finally exit pump 112 through outlet 124. Fluid handling assembly 101 also includes a shroud or cover 112 that protects individual elements 104-112. In the illustrated embodiment, channels formed in shroud 112 provide the fluid connections between the elements, but in other embodiments the fluid connections between elements can be provided by other means, such as tubing. In still other embodiments shroud 112 can be omitted.

Filter and valve assembly 104 includes an inlet 114 and an outlet coupled to fluid connection 116 such that fluid exiting filter and valve assembly 104 flows into pre-concentrator 106. Filter and valve assembly 104 includes a filter to remove particulates from fluid entering through inlet 114. In embodiments of device 100 where one or more of elements 104-112 is a MEMS element, the small scale of parts within the MEMS elements means that fluid entering through inlet 114 might need to be filtered to remove these particles so that the particles do not enter the MEMS elements and either them or render them inoperative. In embodiments of device 100 that include no MEMS components, or where fluid entering inlet 114 contains no particles, for instance because it has been pre-filtered externally to device 100, the filter portion of filter and valve assembly 104 can be omitted.

Filter and valve assembly 104 also includes a valve so that further flow through inlet 114 into fluid handling assembly 101 can be stopped once sufficient fluid has passed through the device. Stopping further flow through inlet 114 prevents dilution of fluids that will flow out of pre-concentrator 106 during later operation of device 100 (see description of operation below). In other embodiments, filter and valve assembly 104 can also include a de-humidifier to remove water vapor from the fluid entering through inlet 114, thus improving the accuracy and sensitivity of device 100.

Pre-concentrator 106 includes an inlet coupled to fluid connection 116 and an outlet coupled to fluid connection 118. Pre-concentrator 106 receives fluid from filter and valve assembly 104 through fluid connection 116 and outputs fluid to gas chromatograph 108 through fluid connection 118. As fluid flows through pre-concentrator 106, the pre-concentrator absorbs certain chemicals from the passing fluid, thus concentrating those chemicals for later separation and detection. In one embodiment of device 100 pre-concentrator 106 can be a MEMS pre-concentrator, but in other embodiments pre-concentrator 106 can be a non-MEMS chip scale device. Further details of an embodiment of a MEMS pre-concentrator are described below in connection with FIG. 2.

Gas chromatograph 108 includes an inlet coupled to fluid connection 118 and an outlet coupled to fluid connection 120. Gas chromatograph 108 receives fluid from pre-concentrator 106 through fluid connection 118 and outputs fluid to detector array 110 through fluid connection 120. As fluid received from pre-concentrator 106 flows through gas chromatograph 108, individual chemicals in the fluid received from the pre-concentrator are separated from each other in the time domain for later input into detector array 110. In one embodiment of device 100 gas chromatograph 108 can be a MEMS gas chromatograph, but in other embodiments gas chromatograph 108 can be a non-MEMS chip scale device. Further details of an embodiment of a MEMS gas chromatograph 108 are described below in connection with FIGS. 3A-3C. Although shown in the drawing as a single chromatograph, in other embodiments gas chromatograph 108 can include multiple individual chromatographs, such as any of the cascaded gas chromatographs shown in FIG. 10A et seq. In an embodiment in which gas chromatograph 108 includes multiple chromatographs, it can be necessary to adjust the number of downstream and/or upstream components in device 100 to coincide with the input or output configuration of the gas chromatograph. For instance, if the cascaded chromatograph 1050 shown in FIG. 10C is used as chromatograph 108 in device 100, it can be necessary to adjust the number of detector arrays 110, pumps 112, and so forth, to correspond to the number of outputs of chromatograph 1050.

Detector array 110 includes an inlet coupled to fluid connection 120 and an outlet coupled fluid connection 122.

Detector array 110 receives fluid from gas chromatograph 108 through fluid connection 120 and outputs fluid to pump 112 through fluid connection 122. As fluid flows through detector array 110, the chemicals that were time-domain separated by gas chromatograph 108 enter the detector array and their presence and/or concentration is sensed by sensors within the detector array. In one embodiment of device 100 detector array 110 can be a MEMS detector array, but in other embodiments detector array 110 can be a non-MEMS chip scale device. Further details of an embodiment of a detector array 110 are described below in connection with FIG. 4. Although shown in the figure as a single detector array, in other embodiments detector array 110 can actually include multiple detector arrays. For example, in an embodiment where gas chromatograph 108 is a cascaded configuration made up of several individual chromatographs, such as cascaded chromatograph 1050 shown in FIG. 10C, it can be necessary to adjust the number of detector arrays to match the output configuration of the cascaded chromatographs.

Pump 112 includes an inlet coupled to fluid connection 122, as well as an outlet coupled to an exhaust 124, such that pump 112 draws fluid from detector array 110 through fluid connections 122 and returns it to the atmosphere through exhaust 124. Pump 112 can be any kind of pump that meets the size and form factor requirements of device 100, provides the desired flow rate and flow rate control, and has adequate reliability (i.e., adequate mean time between failures (MTBF)). In one embodiment, pump 112 can be a MEMS or MEMS-based pump, but in other embodiments it can be another type of pump. Examples of pumps that can be used include small axial pumps (e.g., fans), piston pumps, and electro-osmotic pumps. Although shown in the figure as a single pump, in other embodiments pump 112 can actually be made up of multiple pumps. For example, in an embodiment where gas chromatograph 108 is a cascaded configuration made up of several individual chromatographs, such as cascaded chromatograph 1050 shown in FIG. 10C, it can be necessary to adjust the number of pumps to match the output configuration of the cascaded chromatographs.

Controller 126 is communicatively coupled to the individual elements within fluid handling assembly 101 such that it can send control signals and/or receive feedback signals from the individual elements. In one embodiment, controller 126 can be an application-specific integrated circuit (ASIC) designed specifically for the task, for example a CMOS controller including processing, volatile and/or non-volatile storage, memory and communication circuits, as well as associated logic to control the various circuits and communicate externally to the elements of fluid handling assembly 101. In other embodiments, however, controller 126 can instead be a general-purpose microprocessor in which the control functions are implemented in software. In the illustrated embodiment controller 126 is electrically coupled to the individual elements within fluid handling assembly 101 by conductive traces 130 on the surface or in the interior of substrate 102, but in other embodiments controller 126 can be coupled to the elements by other means, such as optical.

Readout and analysis circuit 128 is coupled to an output of detector array 110 such that it can receive data signals from individual sensors within detector array 110 and process and analyze these data signals. In one embodiment, readout and analysis circuit 128 can be an application-specific integrated circuit (ASIC) designed specifically for the task, such as a CMOS controller including processing, volatile and/or non-volatile storage, memory and communication circuits, as well as associated logic to control the various circuits and communicate externally. In other embodiments, however, readout and analysis circuit 128 can instead be a general-purpose microprocessor in which the control functions are implemented in software. In some embodiments readout and analysis circuit 128 can also include signal conditioning and processing elements such as amplifiers, filters, analog-to-digital converters, etc., for both pre-processing of data signals received from detector array 110 and post-processing of data generated or extracted from the received data by readout and analysis circuit 128.

In the illustrated embodiment, readout and analysis circuit 128 is electrically coupled to detector array 110 by conductive traces 132 positioned on the surface or in the interior of substrate 102, but in other embodiments controller 126 can be coupled to the elements by other means, such as optical means. Readout and analysis circuit 128 is also coupled to controller 126 and can send signals to, and receive signals from, controller 126 so that the two elements can coordinate and optimize operation of device 100. Although the illustrated embodiment shows controller 126 and readout and analysis circuit 128 as physically separate units, in other embodiments the controller and the readout and analysis circuit could be combined in a single unit.

In operation of device 100, the system is first powered up and any necessary logic (i.e., software instructions) is loaded into controller 126 and readout and analysis circuit 128 and initialized. After initialization, the valve in filter and valve unit 104 is opened and pump 112 is set to allow flow through the fluid handling assembly. Fluid is then input to fluid handling assembly 101 through inlet 114 at a certain flow rate and/or for a certain amount of time; the amount of time needed will usually be determined by the time needed for pre-concentrator 106 to generate adequate concentrations of the particular chemicals whose presence and/or concentration are being determined. As fluid is input to the system through inlet 114, it is filtered by filter and valve assembly 104 and flows through elements 104-112 within fluid handling assembly 101 by virtue of the fluid connections between these elements. After flowing through elements 104-112, the fluid exits the fluid handling assembly through exhaust 124.

After the needed amount of fluid has been input through inlet 114, the valve in filter and valve assembly 104 is closed to prevent further input of fluid. After the valve is closed, a heater in pre-concentrator 106 activates to heat the pre-concentrator. The heat releases the chemicals absorbed and concentrated by the pre-concentrator. As the chemicals are released from pre-concentrator 106, pump 112 is activated to draw the released chemicals through gas chromatograph 108 and detector array 110 and output the chemicals through exhaust 124. Activation of pump 112 also prevents backflow through fluid handling assembly 101.

As the chemicals released from pre-concentrator 106 are drawn by pump 112 through gas chromatograph 108, the chromatograph separates different chemicals from each other in the time domain—that is, different chemicals are output from the gas chromatograph at different times. As the different chemicals exit gas chromatograph 108 separated in time, each chemical enters MEMS detection array 110, where sensors in the detection array detect the presence and/or concentration of each chemical. The time-domain separation performed in gas chromatograph 108 substantially enhances the accuracy and sensitivity of MEMS detection array 110, since it prevents numerous chemicals from entering the detection array at the same time and thus prevents cross-contamination and potential interference in the sensors within the array.

As individual sensors within MEMS detection array 110 interact with the entering time-domain-separated chemicals, the detection array senses the interaction and outputs a signal to readout and analysis circuit 128, which can then use the signal to determine presence and/or concentration of the chemicals. When readout and analysis circuit 128 has determined the presence and/or concentration of all the chemicals of interest it can use various analysis techniques, such as correlation and pattern matching, to extract some meaning from the particular combination of chemicals present and their concentrations.

Figure 2A:
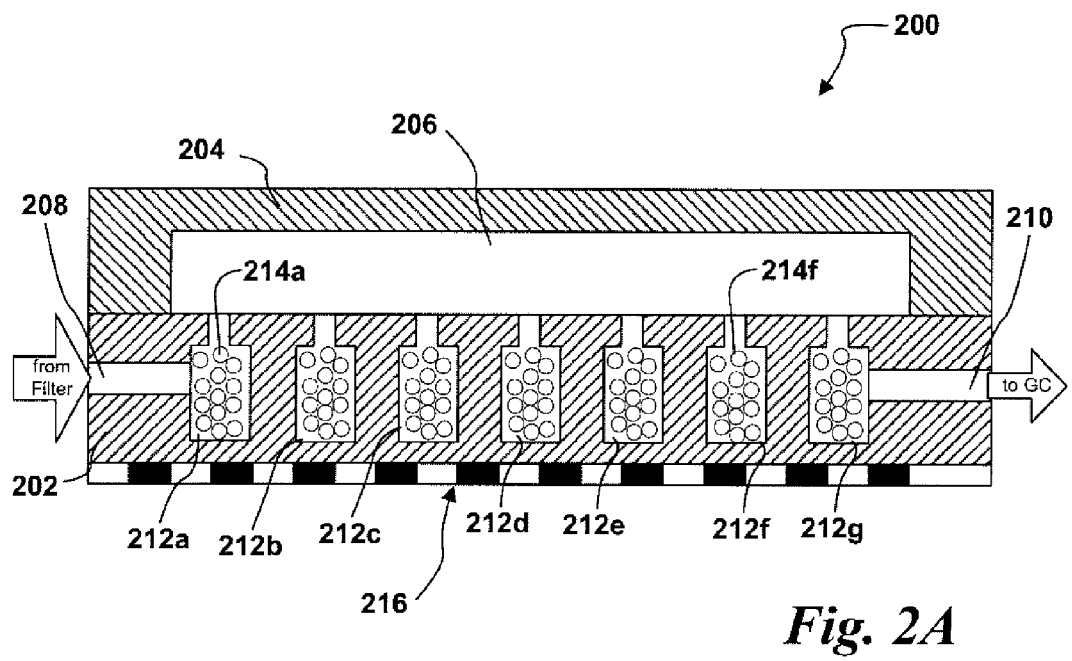
FIG. 2A is a cross-sectional elevation drawing of an embodiment of a MEMS pre-concentrator that can be used in the embodiment of a gas analysis device shown in FIGS. 1A-1B.

FIG. 2A illustrates an embodiment of a MEMS pre-concentrator 200 that can be used as pre-concentrator 106 in device 100. Pre-concentrator 200 includes a substrate 202 having a cover plate 204 bonded thereto and sealed around the perimeter of the substrate to create a cavity 206. Substrate 202 has formed therein an inlet 208 on one side, an outlet 210 on a different side, and pockets 212 having absorbents therein. In one embodiment, substrate 202 is a silicon substrate, but in other embodiments substrate 202 can of course be made of other materials. Heater 216 is formed on the side of substrate 202 opposite the side where cover plate 204 is attached.

In an embodiment where substrate 202 is silicon, inlet 208, outlet 210 and pockets 212 can be formed using standard photolithographic patterning and etching. Although the illustrated embodiment shows seven pockets 212a-212g, the number of pockets needed depends on the number of different chemicals to be absorbed and concentrated, and on the nature of the absorbents used. In an embodiment where each absorbent absorbs only one chemical, the number of pockets 212 can correspond exactly to the number of chemicals to be absorbed and concentrated, but in other embodiments where each absorbent absorbs only one chemical a greater number of pockets can be used to increase the absorption area. In still other embodiments where each absorbent can absorb more than one chemical, a lesser number of pockets can be used.

Each pocket 212 has a corresponding absorbent 214 in its interior—pocket 212a has absorbent 214a, pocket 212b has absorbent 214b, and so on. Although shown in the illustrated embodiment as a granular absorbent, in other embodiments absorbents 214 can be coatings on the walls of pockets 212 or can be a continuous substance that partially or fully fills each pocket 212. Other embodiments can include combinations of granular, wall coatings or continuous filling absorbents. Each absorbent can have a chemical affinity for one or more particular chemicals, meaning that the exact absorbents used will depend on the number and nature of chemicals to be absorbed and concentrated. Examples of absorbents that can be used include cabopack B, cabopack X, etc.

During operation of MEMS pre-concentrator 200 in device 100, fluid from filter and valve assembly 104 enters through inlet 208, passes through absorbent 214a in pocket 212a, and enters cavity 206. Cover plate 204 helps guide fluid entering the cavity 206 into the different pockets 212b-212g and through absorbents 214b-214g, until the fluid, minus the chemicals absorbed by absorbents 214a-214g, exits the pre-concentrator through outlet 210. Once enough fluid has flowed through the pre-concentrator, the valve in filter and valve assembly 104 is closed to prevent further flow through inlet 208. Heater 216 is then activated. Heater 216 heats absorbents 214a-214f, causing them to release the absorbed chemicals through processes such as outgassing. Simultaneously with activating heater 216, or shortly thereafter, pump 112 is activated, drawing the released chemicals out through outlet 210 to gas chromatograph 108.

Figure 2B:
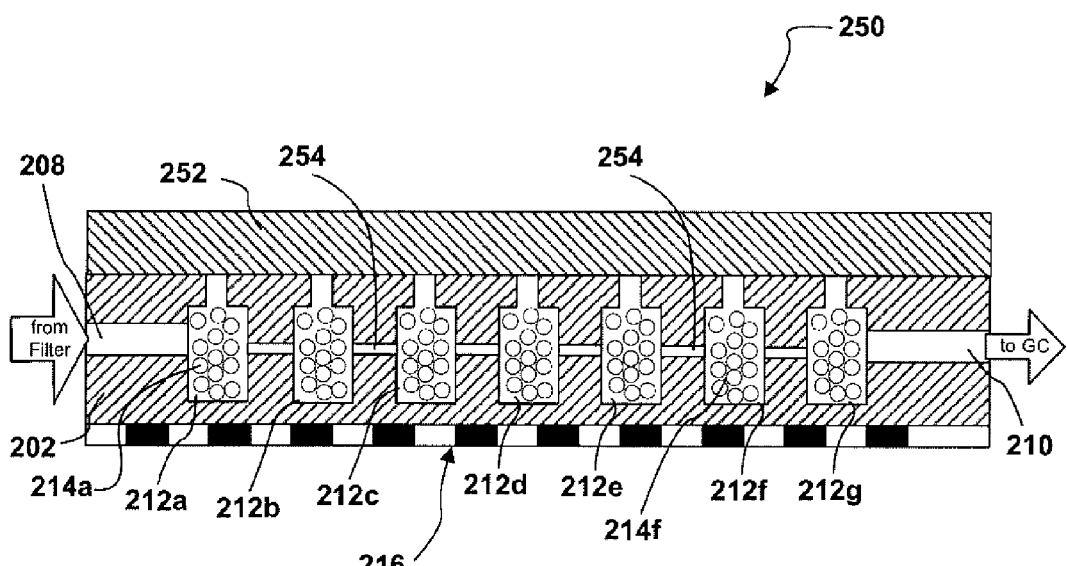
FIG. 2B is a cross-sectional elevation drawing of an alternative embodiment of a MEMS pre-concentrator that can be used in the embodiment of a gas analysis device shown in FIGS. 1A-1B.

FIG. 2B illustrates an alternative embodiment of a MEMS pre-concentrator 250. MEMS pre-concentrator 250 is in many respects similar to MEMS pre-concentrator 200, The primary difference between the two is that in MEMS pre-concentrator 250, the cover plate 252 is directly bonded to the substrate 202 without formation of cavity 206 found in cover plate 204. In one embodiment of MEMS pre-concentrator 250, channels/openings 252 can exist in substrate 202 between the different pockets 212 to allow the fluid to flow through adjacent pockets. In operation of MEMS pre-concentrator 250, fluid enters through inlet 208, passes through the different pockets 212a-212g via the channels/openings 252 between the pockets, and finally exits the pre-concentrator through outlet 210.

Figure 3A:
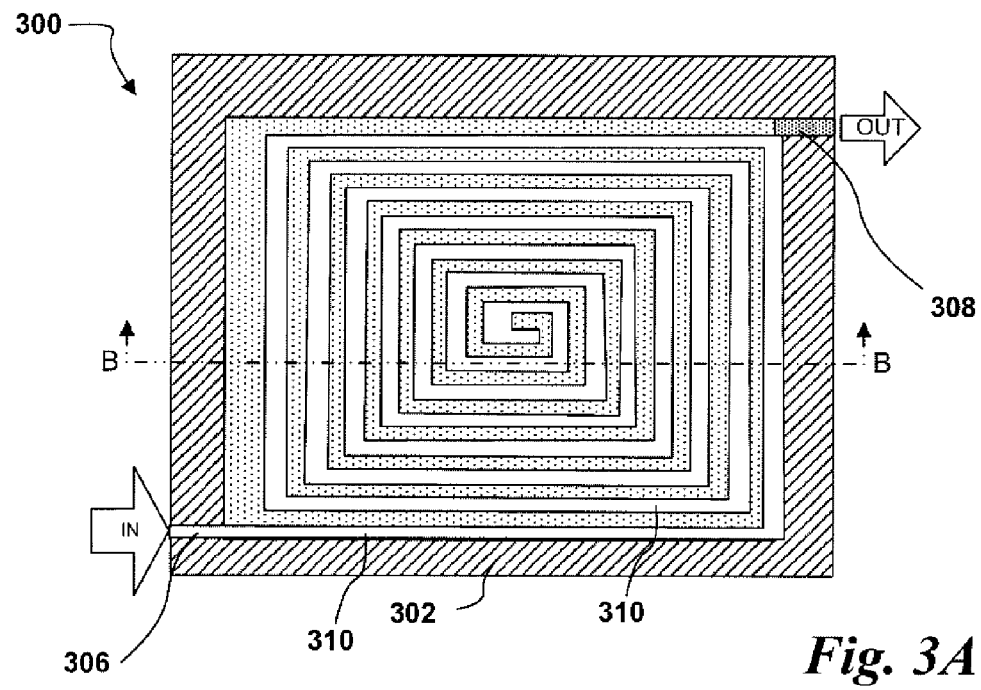
FIG. 3A is a plan view drawing of an embodiment of a MEMS gas chromatograph that can be used in the embodiment of a gas analysis device shown in FIGS. 1A-1B.
Figure 3B:
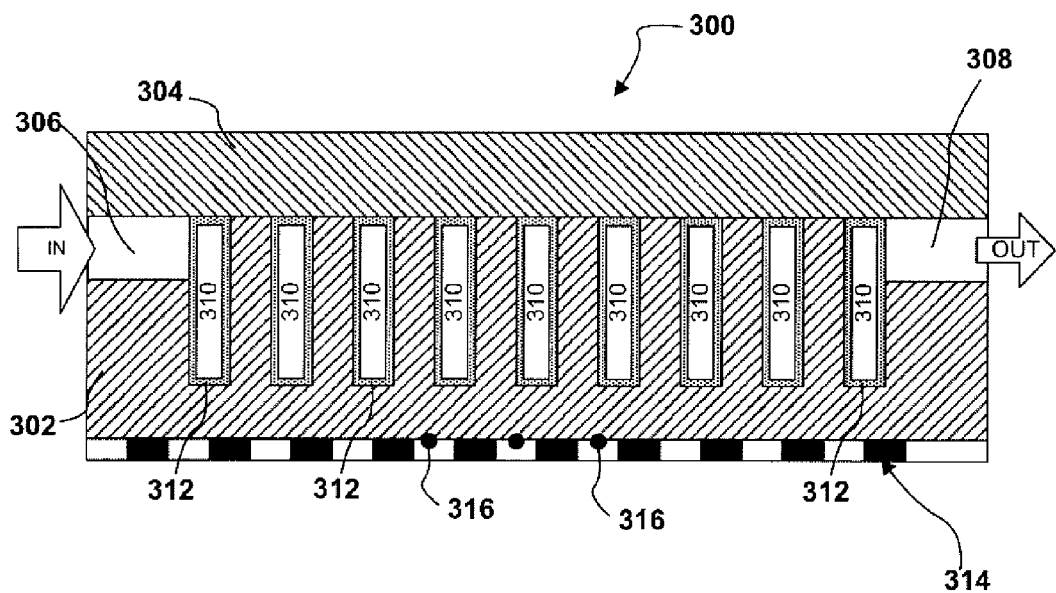
FIG. 3B is a cross-sectional elevation drawing of the embodiment of a MEMS gas chromatograph shown in FIG. 3A, taken substantially along section line B-B.

FIGS. 3A-3B illustrate embodiments of an individual MEMS gas chromatograph 300 that can be used as gas chromatograph 108 in device 100. MEMS gas chromatograph 300 includes a substrate 302 with an inlet 306 on one side, an outlet 308 on a different side, and a separation column 310 having a stationary phase coating on its walls. A cover plate 304 is bonded to substrate 302 to seal column 310. In one embodiment substrate 302 is a silicon substrate, but in other embodiments substrate 302 can of course be made of other materials. In an embodiment where substrate 302 is silicon, inlet 306, outlet 308 and column 310 can be formed using standard photolithographic patterning and etching, such as deep reactive ion etching (DRIE). Temperature control 314 is formed on the side of substrate 302 opposite the side where cover plate 204 is attached. In one embodiment, temperature control is integrated with chromatograph 300 and can include heating elements and/or cooling elements, or elements that are capable of both heating and cooling such as a Peltier device. Temperature control 314 can also include one or more temperature sensors 316 to allow for monitoring and/or feedback control of temperature control 314.

Channel or column 310 provides a continuous fluid path from inlet 306 to outlet 308, and some or all of the walls of column 310 are coated with a stationary phase coating that can interact with the chemicals being separated by the chromatograph or, in other words, the column walls are coated with specific materials that have specific selectivity/separation power for the desired gas analysis. How thoroughly and how fast chemicals are separated from the fluid depend on the stationary phase coating, the overall path length of column 310, and the temperature. For a given stationary phase coating, the longer the column the better the chemical spectrum separation, but a long column also extends the separation time. For a given application, the required path length will therefore usually be determined by a tradeoff among the coating, the column length and the temperature. The illustrated embodiment shows column 310 as a spiral column in which the column path length will depend on the number of coils in the spiral. In other embodiments, however, column 310 can be shaped differently. In one embodiment, column 310 can be between 1 m and 10 m in length, but in other embodiment can be outside this range. In the illustrated MEMS GC, column 310 can be formed by micromachining or micro-electro-mechanical-systems (MEMS) process on silicon wafer, glass wafer, PCB board, or any type of substrate.

During operation of MEMS gas chromatograph 300 in device 100, fluid from pre-concentrator 106 enters through inlet 306 and passes through column 310. As fluid passes through the column 310, the different chemicals in the fluid interact with stationary phase coating 312 at different rates, meaning that the chemicals are separated after traveling through the column, with the chemicals that interact strongly with the stationary phase being separated first and the chemicals that interact weakly with the stationary phase being separated last. In other words, chemicals that interact strongly with the stationary phase are retained longer in the stationary phase, while chemicals that interacted weakly with the stationary phase retained less time in the stationary phase. In some embodiments of gas chromatograph 300 this time-domain separation can occur according to molecular weight (e.g., chemicals with the lowest molecular weight are separated first, followed by higher molecular weights), but in other embodiments it can occur according to other chemical characteristics or other separation mechanisms. As the chemicals are time-domain separated, pump 112 draws them out of MEMS gas chromatograph 300 through outlet 308. Generally, the chemicals exit through outlet 308 in the reverse order of their separation—that is, chemicals with low retention time exit first, while chemicals with higher retention times exit later. After leaving outlet 308, the chemicals enter detector array 110.

Figure 3C:
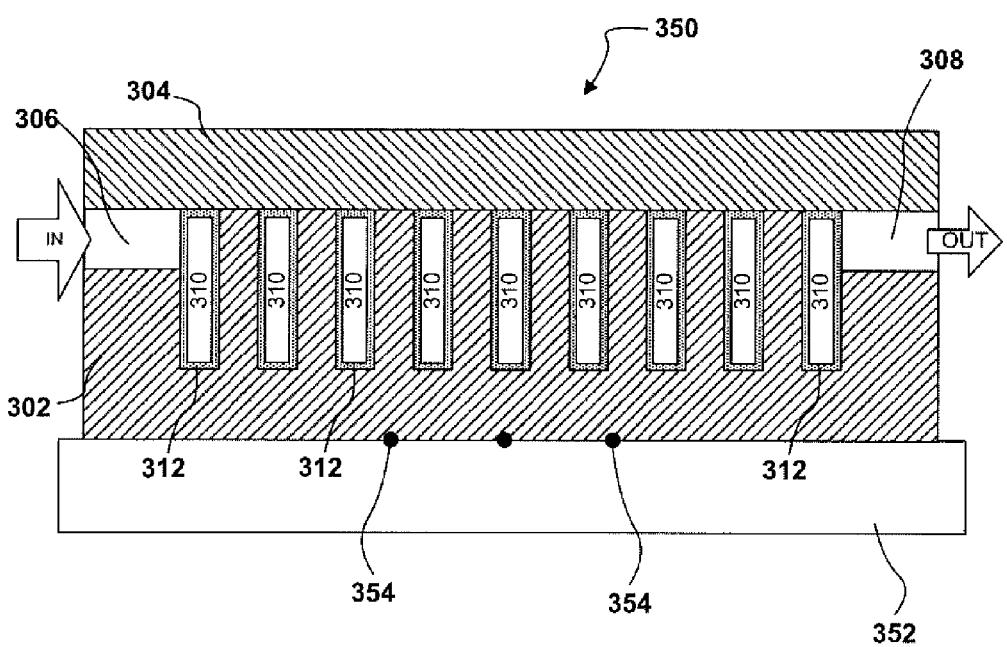
FIG. 3C is a cross-sectional elevation drawing of an alternative embodiment of the MEMS gas chromatograph shown in FIG. 3B.

FIG. 3C illustrates an alternative embodiment of an individual gas chromatograph 350. Gas chromatograph 350 is in most respects similar to gas chromatograph 300 shown in FIG. 3B. The primary difference between gas chromatographs 300 and 350 is the configuration of the temperature control. In gas chromatograph 350, temperature control 352 is not integrated into the chromatograph, but instead is an external component, such as a heating or cooling plate, that is thermally coupled to the chromatograph. Thermal coupling between external temperature control 352 and the chromatograph can be accomplished, for example, using thermally conductive adhesives or with thermal interface materials. As with temperature control 314, temperature control 352 can include one or more temperature sensors 354 to monitor the temperature and/or provide feedback control of the temperature control. Since the GC is small (about 1 inch range in one embodiment, but not limited to this range), faster heating and cooling control can be achieved with either the integrated or external temperature controls.

Figure 3D:
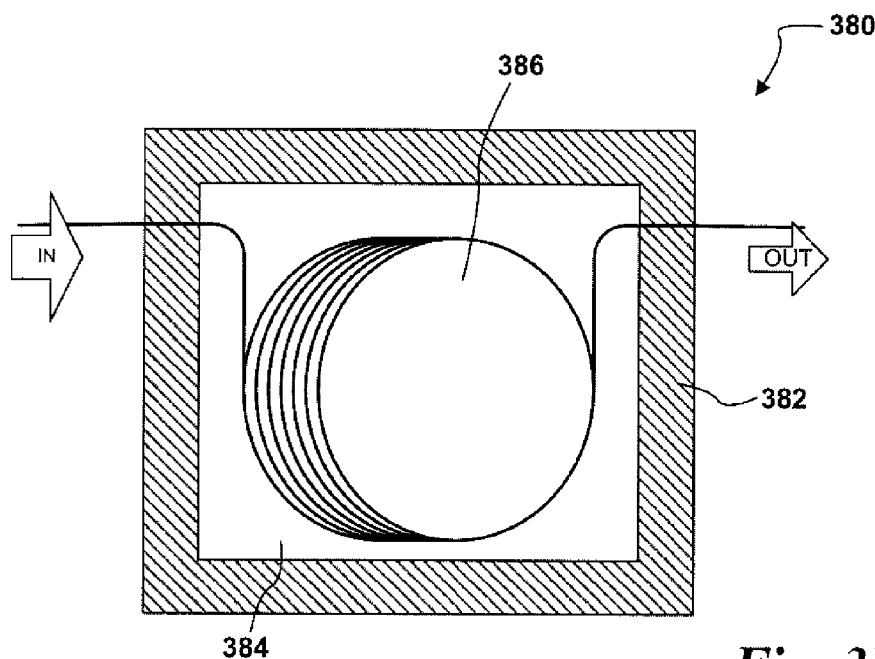
FIG. 3D is a plan view of an alternative embodiment of a gas chromatograph that can be used in the embodiment of a gas analysis device shown in FIGS. 1A-1B.
Figure 3E:
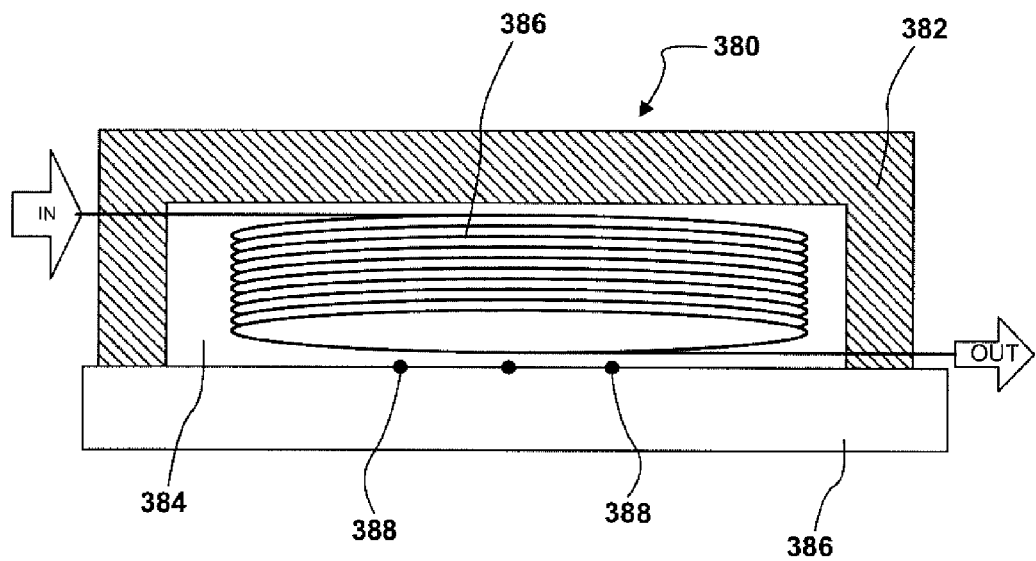
FIG. 3E is a cross-sectional elevation drawing of the embodiment of a gas chromatograph shown in FIG. 3D.

FIGS. 3D and 3E together illustrate an alternative embodiment of an individual gas chromatograph 380. The primary difference between gas chromatographs 380 and 350 is the formation in chromatograph 380 of a conventional chromatography column instead of a MEMS chromatography column. Gas chromatograph 380 includes a substrate 382 having a cavity or opening 384 therein. Positioned within cavity 384 is a chromatography column 386, which in one embodiment can be formed using coiled capillary tube used in conventional chromatography. A temperature control 386 is bonded to substrate 382 to close cavity 384, thus enclosing column 386. In one embodiment, temperature control 386 can be an external temperature control as shown in FIG. 3C, and can include one or more temperature sensors 388 to monitor the temperature and/or provide feedback control of the temperature control. GC 380 can be packaged in a small size to achieve faster heating and cooling control.

Operation of gas chromatograph 380 is similar to gas chromatograph 350 shown in FIG. 3C. The primary difference between gas chromatographs 380 and 350 is the formation of chromatography column. Instead of using MEMS fabricated column chip, the column can be formed by coiled capillary tube used in conventional chromatography. The column is then enclosed by a temperature control 381 as shown in FIG. 3D. Such GC can be packaged in a small size to achieve faster heating and cooling control.

Figure 4A:
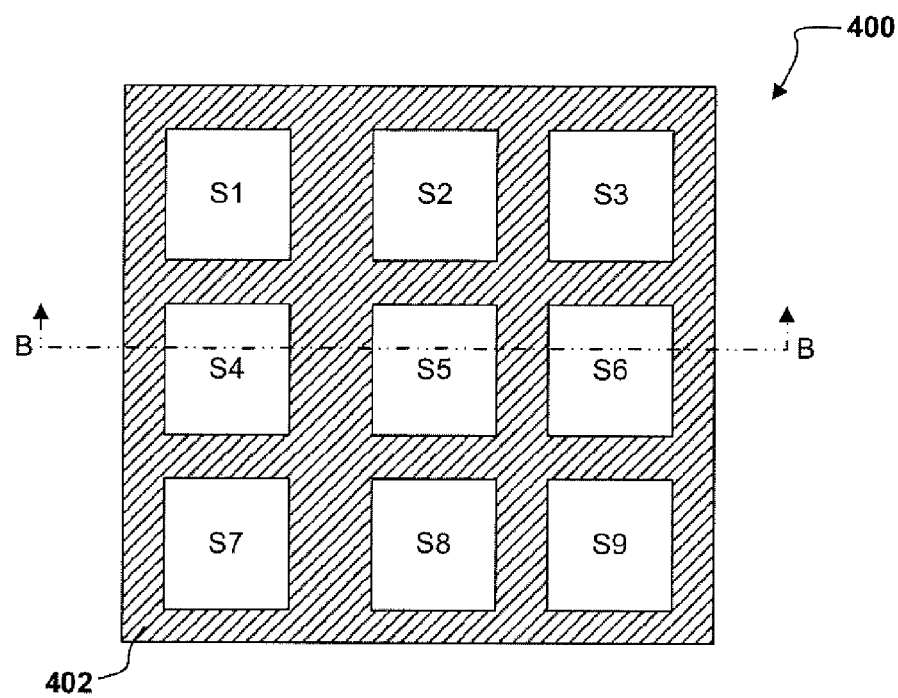
FIG. 4A is a plan view drawing of an embodiment of a detector array that can be used in the embodiment of a gas analysis device of FIGS. 1A-1B.
Figure 4B:
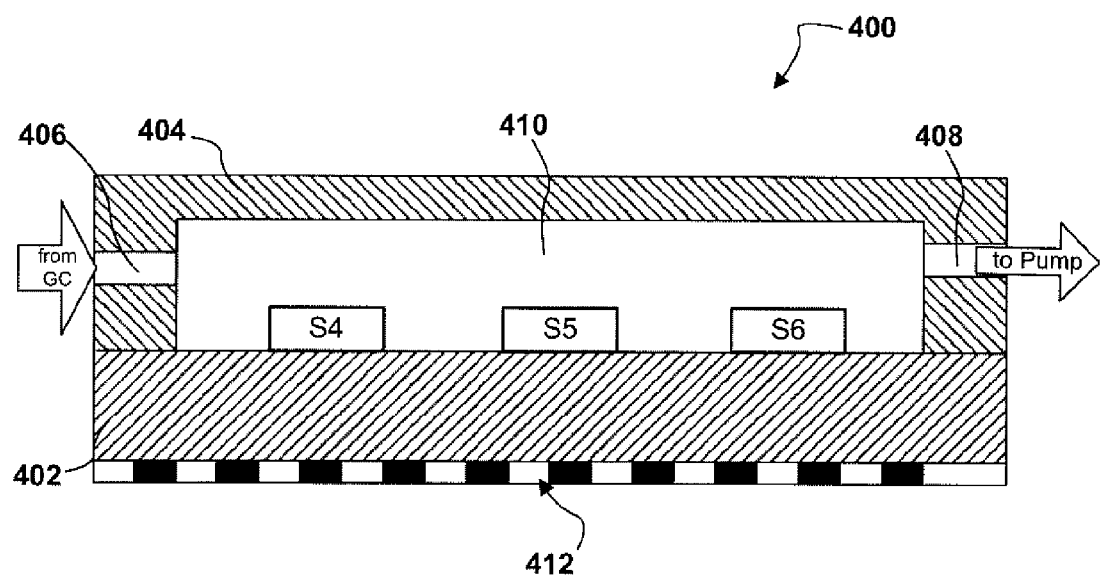
FIG. 4B is a cross-sectional elevation drawing of the embodiment of a detector array shown in FIG. 4A, taken substantially along section line B-B.

FIGS. 4A-4B illustrate an embodiment of a detector array 400 that can be used as detector array 110 in device 100. Detector array 400 includes a substrate 402 with an array of sensors S1-S9 formed thereon. In the illustrated embodiment sensors S1-S9 form a regularly shaped 3-by-3 array of sensors, but in other embodiments the sensor array can have a greater or lesser number of sensors, and the sensors can be arranged in any pattern, regular or irregular.

A cover 404 is bonded to the perimeter of substrate 402 to form a cavity 410 within which sensors S1-S9 are located. Cover 404 also includes an inlet 406 through which fluid can enter from gas chromatograph 108 and an outlet 408 through which fluid can exit to pump 112. A heater 412 is formed on the side of substrate 402 opposite the side where cover 404 is attached to control the temperature of detector array 400, and hence the sensors within the detector array, during operation. Although not shown in the figure, detector array 400 of course includes outputs by which signals generated by sensors S1-S9 can be output for processing.

Each sensor S1-S9 includes a surface with a coating thereon. Each coating used will have an affinity for one or more of the particular chemicals being detected, such that the coating absorbs or chemically interacts with its corresponding chemical or chemicals. The interaction between coating and chemical in turn changes a physical property of the sensor such as resonant frequency, capacitance or electrical resistance, and that changed physical property of the sensor can be measured using a transducer or other measurement device. The particular coatings chosen for sensors S1-S9 will depend on the chemicals that sensor array 110 will be used to detect. The chemical affinity of coatings also varies strongly with temperature, so that the operating temperature range should be considered in selecting coatings. In an embodiment where sensor array 110 will be used to detect volatile organic compounds in human breath—such as benzene, toluene, n-octane, ethylbenzene, m,p-xylene, α-pinene, d-limonene, nonanal, and benzaldehyde, 2-methylhexane, 4-methyloctane, and so on—coatings that can be used in different applications include amorphous copolymers of 2,2-bistrifluoromethyl-4, 5-difluoro-1,3-dioxole (PDD) and tetrafluoroethylene (TFE), PtCl2 (olefin), C8-MPN, etc.

Although the illustrated embodiment has nine sensors, the number of sensors needed depends on the number of different chemicals to be detected, and on the nature of the coatings used on the sensors. In an embodiment where each coating absorbs or chemically interacts with only one chemical the number of sensors can correspond exactly to the number of chemicals to be detected, but in other embodiments it can be desirable to have a given coating on more than one sensor for redundancy. In most cases, however, there is no one-to-one correlation between chemicals to coatings; in other words, each coating reacts with more than one different chemical and the reaction between different chemicals and a given coating will vary in nature and strength. A detector array having sensors with different coatings is therefore useful because the response of the detector array can have different patterns for different gases.

In one embodiment of sensor array 400, sensors S1-S9 are MEMS sensors positioned on the surface of substrate 402, meaning that they are surface micromachined sensors. In other embodiments using MEMS sensors, however, sensors S1-S9 can be bulk micromachined sensors, meaning that at least some of the MEMS sensors are formed within substrate 402 instead of on the surface. Still other embodiments of sensor array 110 using MEMS sensors can include combinations of surface-micromachined and bulk-micromachined sensors. Different types of MEMS sensors can be used, depending on the application and the required sensitivity. Examples of MEMS sensors that can be used include chemiresistors, bulk acoustic wave (BAW) sensors, etc. In other embodiments of detector array 400, one or more of sensors S1-S9 can be a non-MEMS sensor. Examples of non-MEMS sensors that can be used in detector array 400 include quartz crystal microbalance (QCM) or surface acoustic wave (SAW) sensors with quartz or Gallium Arsenide (GaAs) substrates.

During operation of MEMS detector array 400 in device 100, fluid from gas chromatograph 108 enters through inlet 406 and passes into cavity 410. Fluid entering cavity 410 carries time-domain separated chemicals. As each chemical enters cavity 410 it interacts with one or more sensors whose coating has an affinity for that chemical. The interaction of the chemical with the sensor is sensed and measured, and the presence and concentration of the particular chemical can be extracted. As more fluid flows into cavity 410, the first chemical is pushed out of cavity 410 through outlet 408 and fluid with the next time-domain-separated chemical enters cavity 410, interacts with the sensor array and is measured. This process continues until all the time-domain-separated chemicals from gas chromatograph 108 have flowed through detector array 110. In some embodiments where the affinity of the coatings for their chemicals is not strong, detector array 110 can be re-usable: after all time-domain-separated chemicals have been sensed, heater 412 can be activated to heat the sensors and cause the coatings to release the respective chemicals with which they interacted, making the interaction reversible. In embodiments where the affinity of each coating for its chemicals could be strong, heating of the sensor array could help release the partially absorbed gas from the coating materials.

Figure 5:
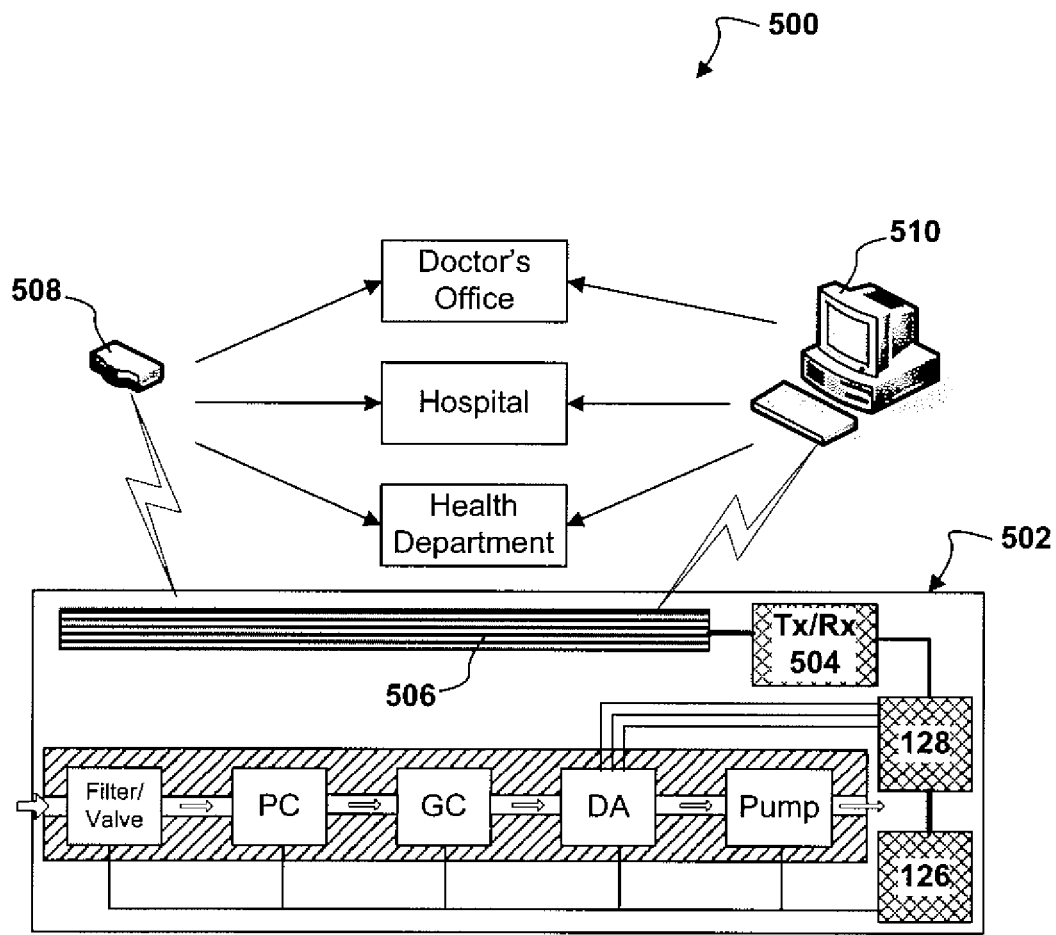
FIG. 5 is a schematic diagram of an alternative embodiment of a gas analysis device and an embodiment of a system using the embodiment of the gas analysis device.

FIG. 5 illustrates an embodiment of a system 500 using an alternative embodiment of a MEMS-based gas analysis device 502. Device 502 is in most respects similar to device 100. The primary difference between device 502 and device 100 is the presence in device 502 of a wireless transceiver circuit 504 and an antenna 506 mounted on substrate 102. Wireless transceiver circuit 504 can both transmit (Tx) data and receive (Rx) data and is coupled to reading and analysis circuit 128 and antenna 506.

In one embodiment of system 500, transceiver 504 can be used to wirelessly transmit raw data from reading and analysis circuit 128 to one or both of a router 508 and a computer 510. When transmitted to router 508, the data can then be re-transmitted to another destination for analysis. For example, in an application where device 502 is used for health-related chemical analysis, data sent to router 508 can be re-transmitted to one or more of a doctor's office, a hospital, a government health department, or someplace else for analysis and interpretation. After analysis is complete, or if there is a problem with the data, the doctor's office, hospital or health department can send instructions to device 502 through router 508, antenna 506 and transceiver 504 to signal the result, to try to fix or improve the data, or to signal that the test must be performed again.

Continuing with the same health-care example, in the same or another embodiment of system 500, wireless transceiver 504 can be used to transmit raw data to computer 510. Computer 510 can either forward the raw data to a doctor, hospital, etc., as did the router, or can analyze the data with software installed thereon to provide extract information from the data, such as one or more possible medical diagnoses, and provide the extracted information to the user of device 502. When it provides analysis and medical diagnoses, computer 510 can also forward the diagnosis, alone or with the analysis and raw data, on to the doctor, hospital, etc. As with the router, the doctor's office, hospital or health department can send instructions to device 502 through computer 510, antenna 506 and transceiver 504 to try to fix or improve the data, to signal that the test must be performed again, and so on.

Again continuing with the same health-care example, in still another embodiment of system 500 the raw data can be processed, and information such as potential diagnoses extracted from the data, by reading and analysis circuit 128. The potential diagnoses determined by reading and analysis circuit 128 can then be sent to computer 510 to be reviewed by the user and/or forwarded, or can be immediately forwarded alone or with the supporting raw data to the doctor's office, etc.

Figure 6:
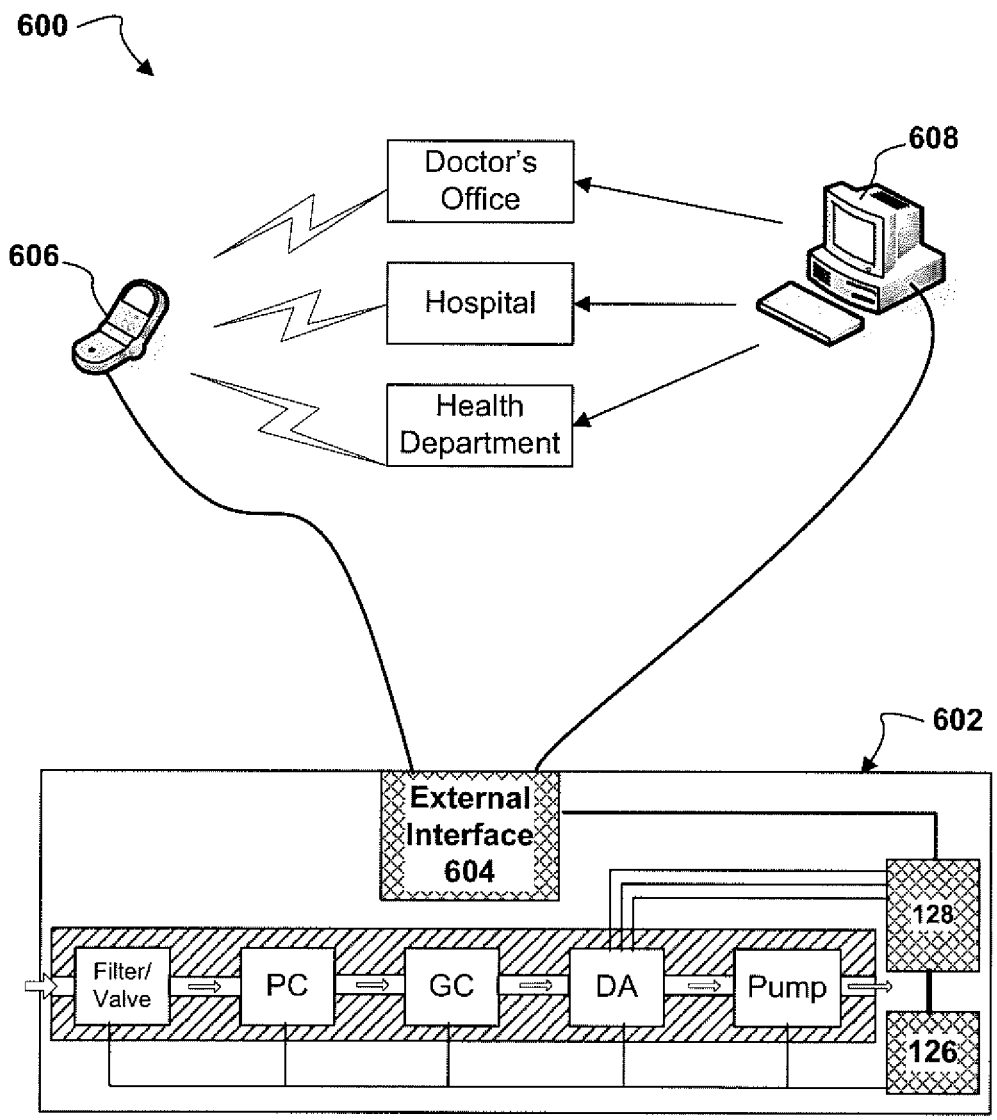
FIG. 6 is a schematic diagram of another alternative embodiment of a gas analysis device and an embodiment of a system using the embodiment of the gas analysis device.

FIG. 6 illustrates an embodiment of a system 600 using an alternative embodiment of a MEMS-based gas analysis device 602. Device 602 is in most respects similar to device 502. The primary difference between device 502 and device 602 is that the wireless transceiver circuit 504 and antenna 506 are replaced with a hardware data interface 604 coupled to reading and analysis circuit 128. In one embodiment, hardware data interface 604 could be a network interface card, but in other embodiments hardware data interface can be an Ethernet card, a simple cable plug, etc. External devices can be connected to device 602 through traditional means such as cables. Although it has a different communication interface, device 602 and system 600 have all the same functionality as device 502 and system 500. As with system 500, in system 600 MEMS-based gas analysis device 602 can transmit data to, and receive data from, one or both of a computer 608 and a wireless device 606, such as a cell phone or personal digital assistant (PDA). When transmitted to wireless device 606 the data can then be forwarded to a doctor's office, hospital, or government health department, and the recipients of the data can in turn send data or instructions back to gas analysis device 602 through the wireless device. As in system 500, when data is transmitted to computer 608 it can be forwarded or can be analyzed by the computer and the result displayed for the user and/or forwarded, and instructions can be transmitted to device 602 through computer 608. Similarly, the data from gas analysis device 602 can be analyzed by reading and analysis circuit 128. After analysis by circuit 128, the extracted information (e.g., one or more diagnoses) and/or the raw data can be forwarded via the hardware data interface 604.

Figure 7:
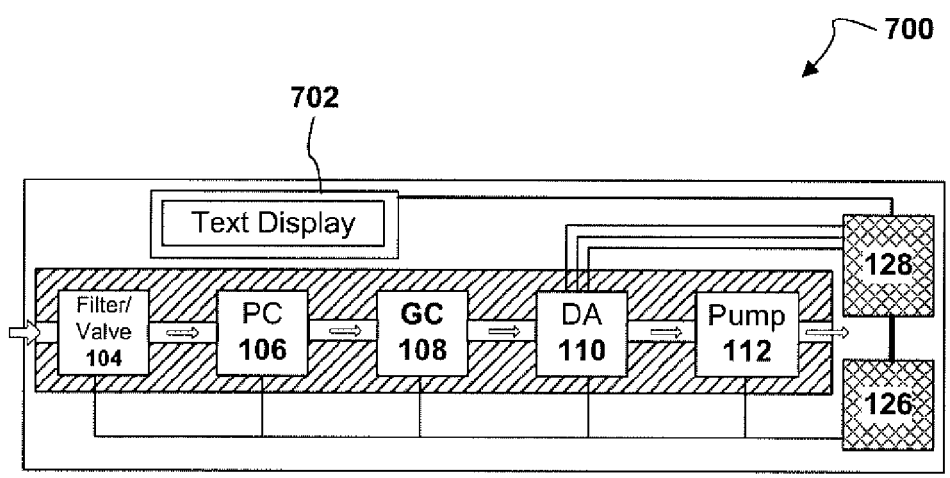
FIG. 7 is a plan-view schematic diagram of an additional alternative embodiment of a gas analysis device.

FIG. 7 illustrates an alternative embodiment of a MEMS-based gas analysis device 700. Device 700 is in most respects similar to device 100. The primary difference between system 700 and device 100 is that device 700 includes an on-board display 702 for conveying to a user the results of the analysis performed by reading and analysis circuit 128.

The illustrated embodiment uses an on-board text display 702, for example an LCD screen that can convey text information to a user. For example, in a health care example display 702 could be used to display the test results in analog numbers indicating the situation of patients. Display 702 could indicate a positive or negative diagnosis, could indicate probabilities of a given diagnosis, or could indicate the raw data from the detector array. In another health care embodiment, simpler displays can be used, such as one with three lights that indicate a positive, negative, or indeterminate result depending on which light is switched on.

Figure 8:
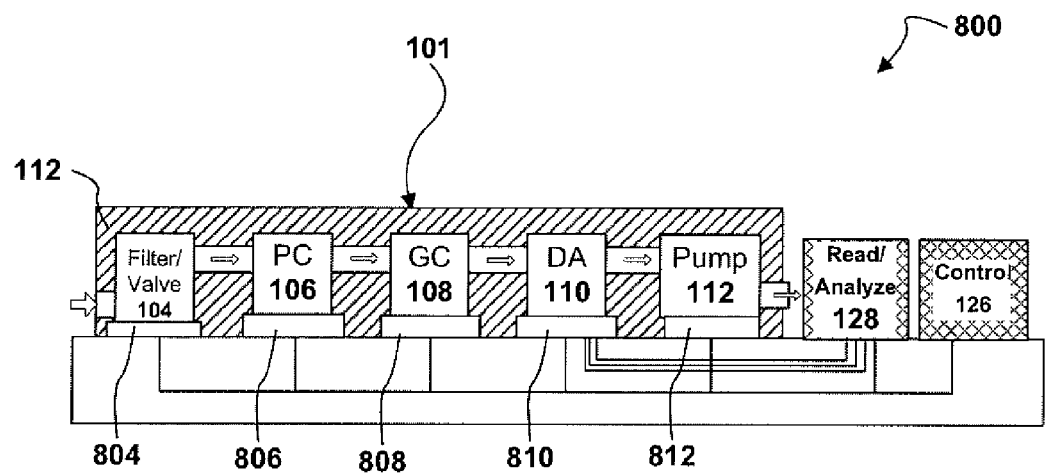
FIG. 8 is a plan-view schematic diagram of an additional alternative embodiment of a gas analysis device.

FIG. 8 illustrates an alternative embodiment of a MEMS-based gas analysis device 800. Device 800 is in most respects similar to device 100. The primary difference between device 800 and device 100 is that in device 800 one or more elements of fluid handling assembly 101 are replaceable. In the illustrated embodiment, the elements are made replaceable by mounting them onto substrate 102 using sockets: filter and valve assembly 104 is mounted to substrate 102 by socket 804, pre-concentrator is mounted to substrate 102 by socket 804, gas chromatograph 108 is mounted to substrate 102 by socket 808, detector array 110 is mounted to substrate 102 by socket 810, and pump 112 is mounted to substrate 102 by socket 812. In one embodiment, sockets 804-812 are sockets such as zero insertion force (ZIF) sockets that permit easy replacement by a user, but in other embodiments other types of sockets can be used. Although the illustrated embodiment shows all the components of fluid handling assembly 101 being replaceable, in other embodiments only some of the components such as pump 112 and detector array 110 can be made replaceable.

Figure 9:
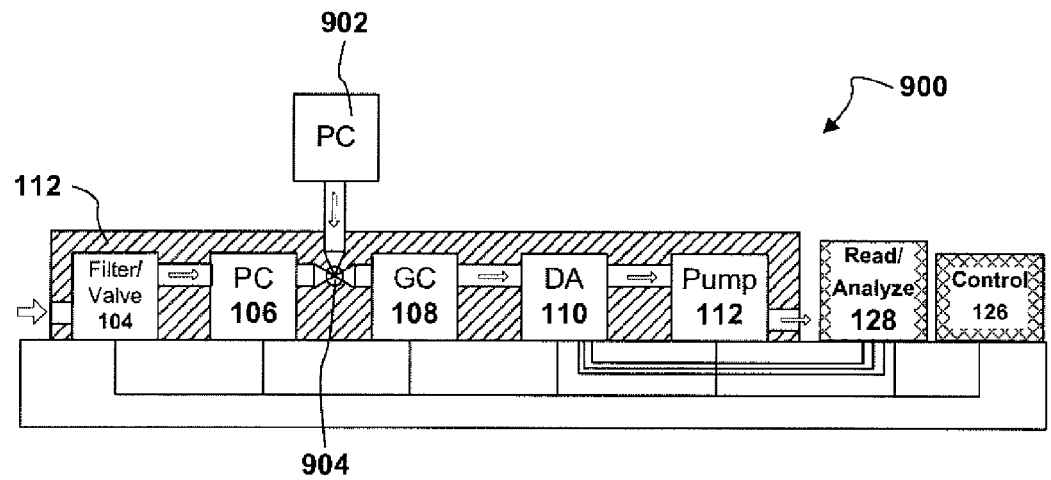
FIG. 9 is a plan-view schematic diagram of an additional alternative embodiment of a gas analysis device.

FIG. 9 illustrates an alternative embodiment of a MEMS-based gas analysis device 900. Gas analysis device 900 is in most respects similar to device 100. The primary difference between device 900 and device 100 is that device 900 includes provisions for an external pre-concentrator 902 (i.e., a pre-concentrator not mounted on substrate 102). In the embodiment shown, a valve 904 is placed between pre-concentrator 106 and gas chromatograph 108, and provisions are made to attach external pre-concentrator 902 to the valve. Valve 904 allows the user to use external pre-concentrator 902 instead of, or in addition to, on-board pre-concentrator 106. In one embodiment external pre-concentrator 902 is a breath collection bag, but in other embodiments it can be something different. In an alternative embodiment of device 900 (not shown), pre-concentrator 106 can be permanently removed and replaced by external pre-concentrator 902. In another embodiment where external pre-concentrator 902 replaces pre-concentrator 106, instead of inserting a valve between pre-concentrator 106 and gas chromatograph 108, external pre-concentrator 902 can be coupled upstream of the filter and valve assembly 104.

FIGS. 10A-10F illustrate embodiments of cascaded gas chromatographs (CGCs) that can be used, for example, as gas chromatograph 108 in gas analysis system 100. As explained previously, GC column coatings are usually optimized for specific temperatures and chemicals, so that no single GC can separate a large array of chemicals, even by varying its temperature. Cascading multiple GCs with individual temperature control can provide complementary gas separation between GCs, resulting in better overall separation and a better, more defined chemical spectrum.

Figure 10A:
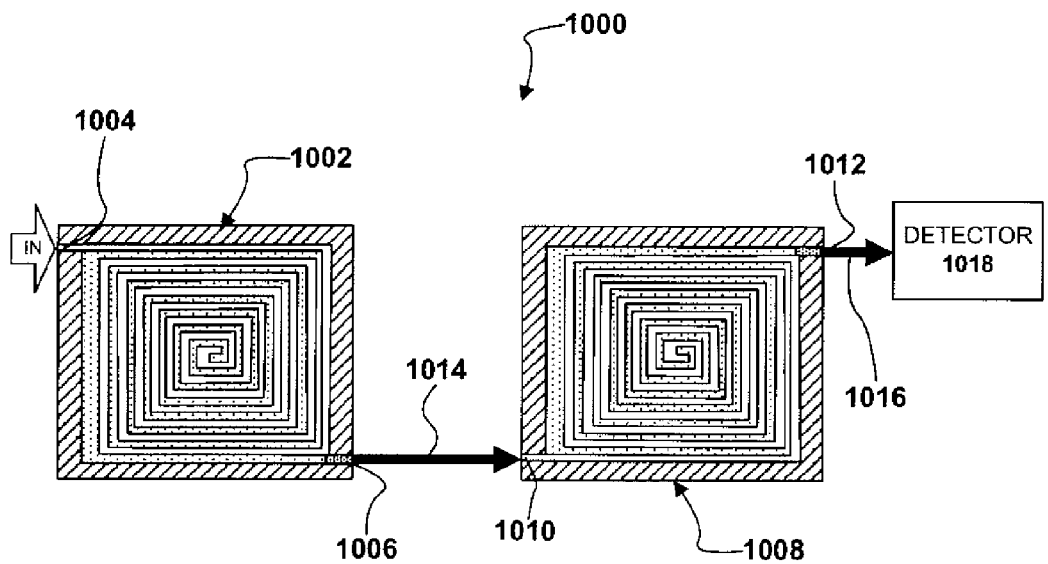
FIG. 10A is a plan-view schematic of an embodiment of a cascaded gas chromatograph.

FIG. 10A illustrates a cascaded gas chromatograph (CGC) 1000 that includes a first gas chromatograph (GC) 1002 coupled to a second GC 1008. In the illustrated embodiment, GCs 1002 and 1008 are coupled in series such that outlet 1006 of GC 1002 is coupled to inlet 1010 of GC 1008 by a fluid connection 1014. Outlet 1012 of GC 1008 is coupled to a detector 1018 by a fluid connection 1016, although in other embodiments outlet 1012 could be coupled to some entirely difference component. Although the embodiment illustrated in the figure has only two GCs, in other embodiments one or more additional GCs, as well as other components such as additional fluid connections, flow splitters, three-way valves detectors and switch valves, can be added to form a larger cascade of GCs.

In some embodiments, GCs 1002 and 1008 can have the same characteristics, but in other embodiments GCs 1002 and 1008 need not have the same characteristics and can have different column lengths, column coatings, operating temperatures, etc. In one embodiment, for example, GC 1002 can be coated with material A, which can be especially selective to polar or non-polar chemicals, and can have its optimum temperature control profile to separate specific chemicals. Meanwhile, GC 1008 can have a different column length and can be coated with another material B, which can separate different chemicals that GC 1002 cannot resolve (separate); in other words, GC 1008 is complementary to GC 1002. Since each GC in the configuration can has its own temperature control, GC 1008 can be optimized to separate the remaining gases of interest that are not resolved (separated) by GC 1002. The separated gases can then be detected by detector 1018 at output of GC 1008.

In the illustrated embodiment, GCs 1002 and 1008 are MEMS gas chromatographs with individual temperature controls, such as those shown in FIG. 3B or 3C, but in other embodiments they can be traditional GCs with individual and independent temperature controls, such as the capillary column chromatographs shown in FIGS. 3D-3E and 12A-12C. The individual temperature controls allow the operating temperature of each GC to be controlled independently of the other. In other embodiments GCs 1002 and 1008 need not be of the same type—that is, CGC 1000 can include both MEMS and non-MEMS chromatographs. In some embodiments both chromatographs can have the same kind of temperature control, but in other embodiments both chromatographs need not have the same temperature control; for example, in the illustrated embodiment with two MEMS chromatographs, GC 1002 can have an integrated temperature control as shown in FIG. 3B, while GC 1008 has an external temperature control, as shown in FIGS. 3C-3E. In one embodiment, detector 1018 is a detector array as shown in FIGS. 4A-4B, but in other embodiments it can be a different type of detector.

In operation of CGC 1000, a carrier fluid having one or more chemicals therein enters GC 1002 through inlet 1004 and flows through the GC's column. The GC's temperature control is used to establish and/or maintain the temperature of GC 1002 at the temperature needed for the desired separation of the chemicals from the fluid. The carrier fluid, with any chemicals not resolved (separated) by GC 2002, exits through outlet 1006 into fluid connection 1014. Fluid connection 1014 carries the fluid into GC 1008, where the fluid flows through the GC's column and some or all of the unresolved chemicals remaining after GC 1002 are separated. As with GC 1002, the temperature control of GC 1008 is used to establish and/or maintain the temperature needed for the desired separation of the chemicals from the fluid. Outlet 1012 of GC 1008 is coupled to a detector, which can then be used to detect the chemicals separated from the carrier fluid by the two GCs. In another embodiment of the operation of GC 1000, each individual GC's temperature does not need to be fixed at certain temperature. Each GC can be controlled to have different dynamic temperature ramping profile to achieve desire chemical separation.

Figure 10B:
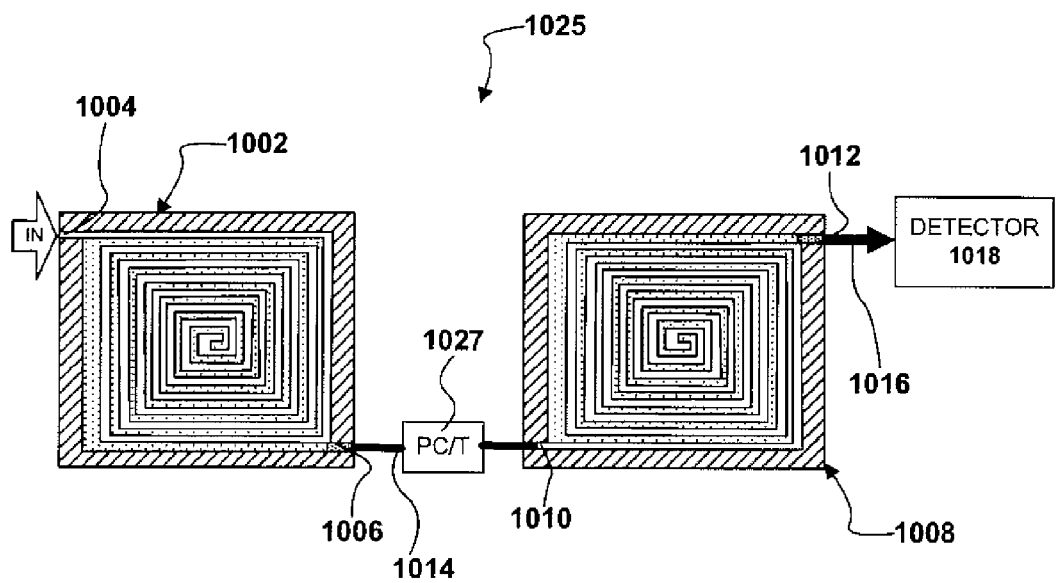
FIG. 10B is a plan-view schematic of an alternative embodiment of a cascaded gas chromatograph.
Figure 10C:
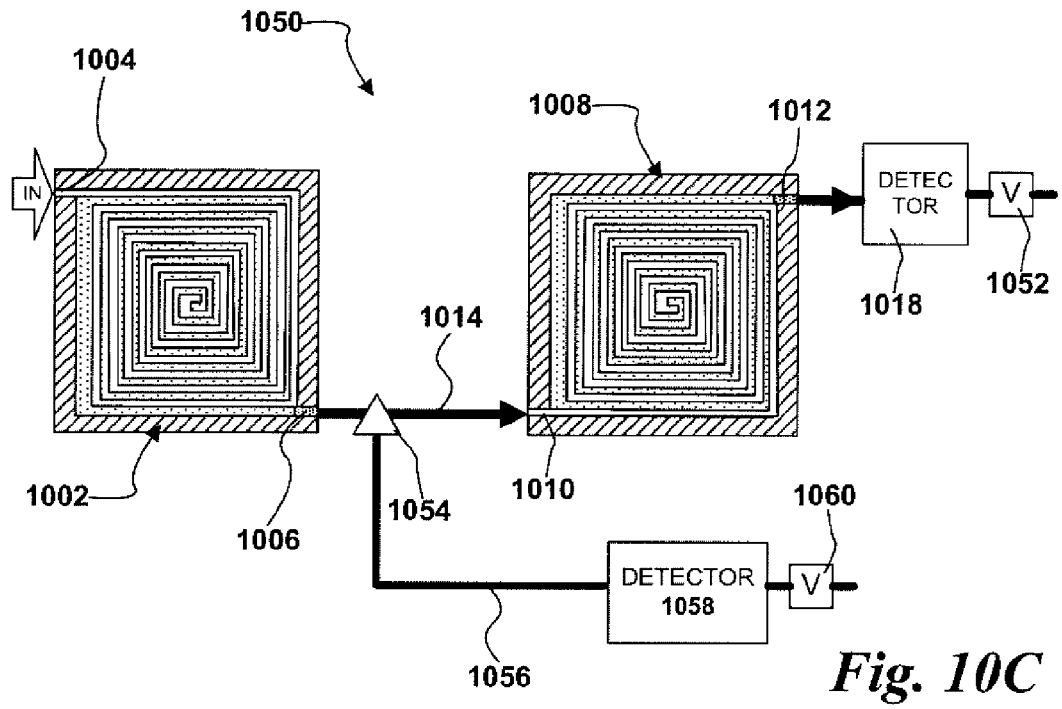
FIG. 10C is a plan-view schematic of another alternative embodiment of a cascaded gas chromatograph.

FIG. 10B illustrates an alternative embodiment of a CGC 1025. CGC 1025 is in most respects similar to CGC 1000. The primary difference between the two is the presence in CGC 1025 of a pre-concentrator and/or trap (PC/T) 1027 coupled into the fluid connection 1014. In one embodiment, PC/T 1027 can be a chip or other MEMS-scale device through which fluid flows when traveling in fluid connection 1014 from outlet 1006 to inlet 1010, but in other embodiments it can be a non-MEMS device. CGC 1025 operates similarly to CGC 1000, but in GC 1025 PC/T 1027 can be periodically cooled and/or heated to trap and release separated chemicals with higher concentration and short spectrum before they enter GC 1008. GC 1008 can then further separate the chemicals as described for CGC 1000 above. With the addition of PC/T 1027, the gases spectrum can be narrower with higher gas concentration for the detector sensing.

FIG. 10C illustrates an alternative embodiment of a CGC 1050 with multiple flow paths. CGC 1050 is similar to CGC 1000 in that GCs 1002 and 1008 are coupled such that outlet 1006 of GC 1002 is coupled to inlet 1010 of GC 1008 by a fluid connection 1014. Outlet 1012 of GC 1008 is coupled to a detector 1018 by a fluid connection 1016, and detector 1018 is further coupled to a switch valve 1052 by a further fluid connection. In CGC 1050, an additional fluid connection 1056 is coupled to fluid connection 1014 by a flow splitter or three-way valve 1054. In addition to being coupled to fluid connection 1014, fluid connection 1056 is coupled to the inlet of detector 1058, and a switch valve 1060 is fluidly coupled to the outlet of detector 1058. Switch valves 1018 and 1058 can control whether gases can flow to the corresponding detectors for gas sensing. Detectors 1018 and 1058 can be different and have specific sensitivity to different gases. Although the embodiment illustrated in the figure has only two GCs, in other embodiments one or more additional GCs, as well as other components such as additional fluid connections, flow splitters, three-way valves detectors and switch valves, can be added to form a cascaded array of GCs.

CGC 1050 has different modes of operation, depending on whether element 1054 is a flow splitter or a three-way valve. In an embodiment where element 1054 is a flow splitter, a carrier fluid having one or more chemicals therein enters GC 1002 through inlet 1004 and flows through the GC's column. The GC's temperature control is used to establish and/or maintain the temperature of GC 1002 at the temperature needed for the desired separation of the chemicals from the fluid. The carrier fluid, with any chemicals not resolved (separated) by GC 1002, exits through outlet 1006 into fluid connection 1014. A portion of the fluid carried by fluid connection 1014 is directed into GC 1008, and a portion of the fluid is directed into fluid connection 1056. The portion entering GC 1008 flows through the GC's column and some or all of the unresolved chemicals remaining after GC 1002 are separated. As with GC 1002, the temperature control of GC 1008 is used to establish and/or maintain the temperature needed for the desired separation of the chemicals from the fluid. Outlet 1012 of GC 1008 is coupled to detector, which can then be used to detect the chemicals separated from the carrier fluid by the two GCs. The portion of fluid directed into fluid connection 1056 flows to detector 1058. When both switch valves 1052 and 1060 are opened, partial gases that are separated by GC 1002 can be directly sensed by detector 1058, while partial gases are fed into GC 1008 for further separation and sensing by detector 1018. In another mode of operation where element 1054 is a flow splitter, only one of switch valves 1052 and 1060 is opened. With only one switch valve open, full gas can flow path can be switched between detectors 1018 and 1058 without losing partial gases (lower gases amount to be sensed). In an embodiment in which element 1054 is a three-way valve, the three-way valve can be used to control the flow and switch valves 1052 and 1060 can be eliminated.

Figure 10D:
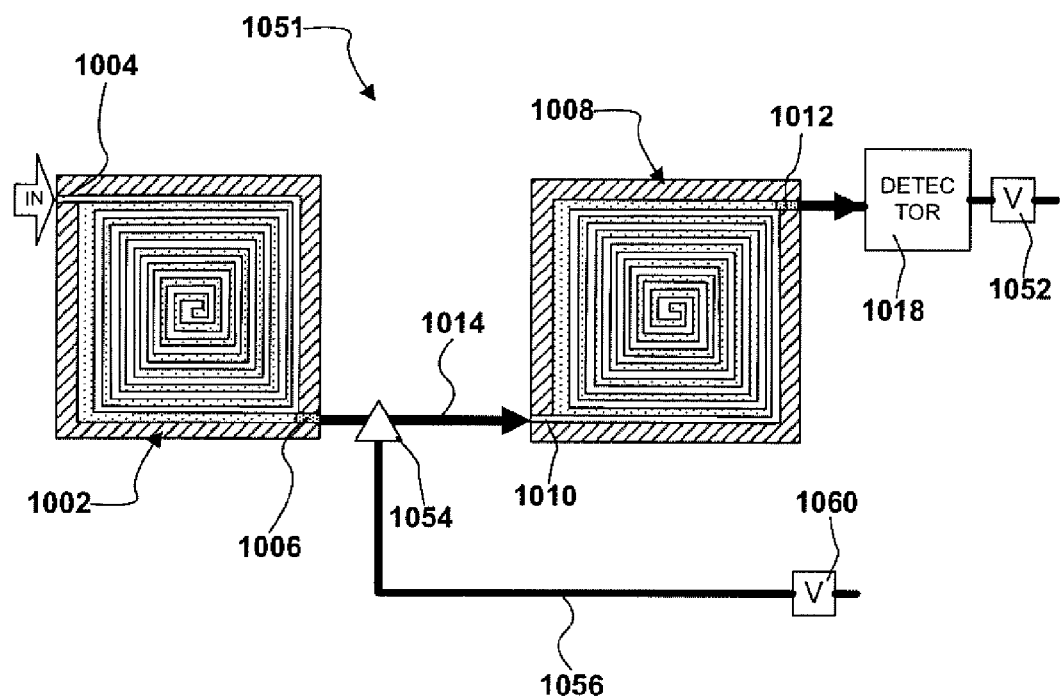
FIG. 10D is a plan-view schematic of another alternative embodiment of a cascaded gas chromatograph.

FIG. 10D illustrates an alternative embodiment of a CGC 1051. CGC 1051 is in most respects similar to CGC 1050. The principal difference between the two is the omission of detector 1058 from CGC 1051. For operations in which some chemical gases exiting from GC 1002 are not needed, CGC 1051 can be used to remove the unwanted chemicals by switching or directing the chemicals exiting GC 1002 into fluid connection 1056 and discarding them.

Figure 10E:
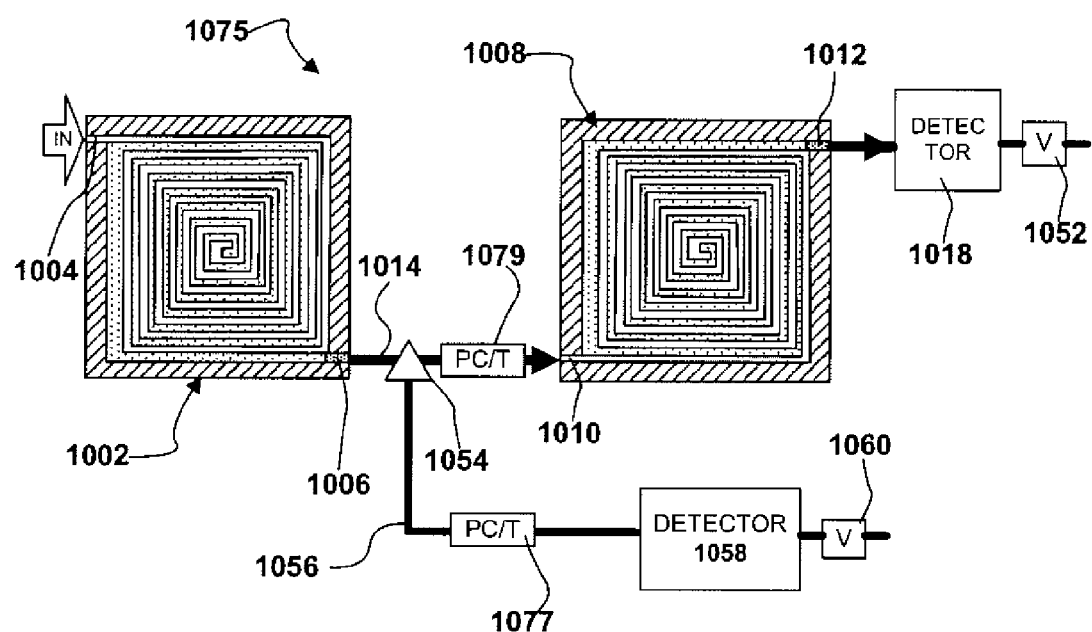
FIG. 10E is a plan-view schematic of another alternative embodiment of a cascaded gas chromatograph.

FIG. 10E illustrates an alternative embodiment of a CGC 1075. CGC 1075 is in most respects similar to CGC 1050. The primary difference between the two is the presence in CGC 1075 of pre-concentrator and/or trap (PC/T) 1079 coupled to fluid connection 1014 and pre-concentrator and/or trap (PC/T) 1077 coupled to fluid connection 1056. In one embodiment, PC/Ts 1077 and 1079 can be pre-concentrator and/or trap chips or other MEMS-scale device through which fluid flows when traveling through fluid connections 1014 and 1056, but in other embodiments PC/Ts 1077 and 1079 need not be MEMS-scale devices. In still other embodiments, PC/Ts 1077 and 1079 can be different types of pre-concentrators or traps. CGC 1075 operates in a manner similar to CGC 1050, except that PC/Ts 1077 and 1079 are used to periodically trap/release narrow and higher concentration gas spectrums for detector sensing.

Figure 10F:
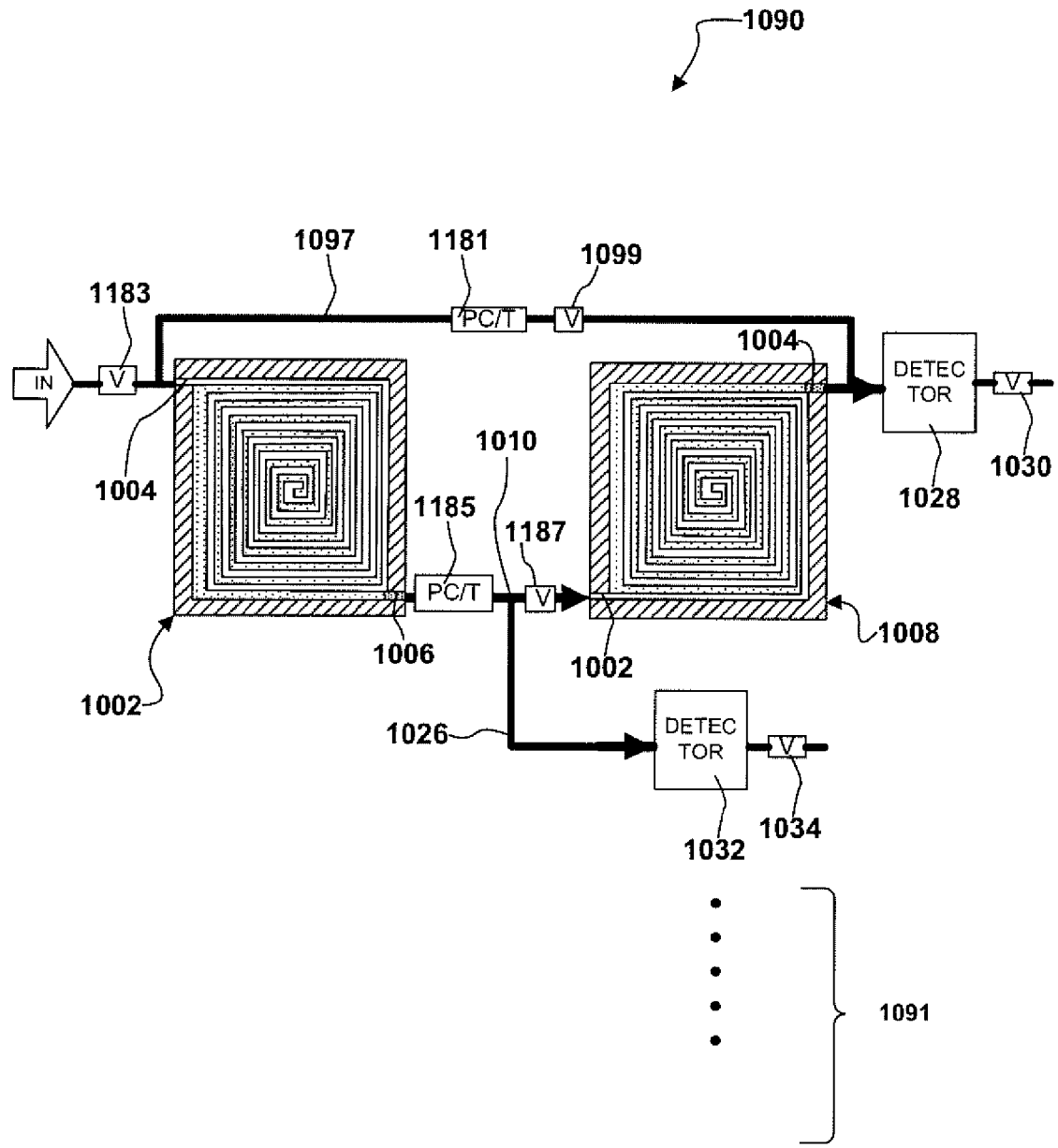
FIG. 10F is a plan-view schematic of another alternative embodiment of a cascaded gas chromatograph.

FIG. 10F illustrates an alternative embodiment of a CGC 1090. CGC 1090 is similar in most respects to CGC 1075. The primary difference between CGC 1090 and CGC 1075 is the addition in CGC 1090 of a fluid connection 1097 between the outlet of GC 1008 and the inlet of GC 1002. A pre-concentrator and/or trap (PC/T) 1181 and switch valve 1099 are coupled in fluid connection 1097. Fluid connection 1097 allows gases to re-circulate between two or more GCs to increase the effective GC column length without having to physically lengthen the GC column or add additional GCs in series. An additional switch valve 1187 is also coupled to fluid connection 1010 between the outlet of GC 1002 and the inlet of GC 1008. In the illustrated embodiment, PC/T 1077 (see FIG. 10E) has been removed from fluid connection 1026, but in other embodiments of CGC 1090 it could be reinserted. Although the embodiment illustrated in the figure has only two GCs, in other embodiments one or more additional GCs or detectors, as well as other components such as additional fluid connections, flow splitters, three-way valves detectors and switch valves, can be added to form a cascaded array of GCs, as indicated by dots 1091.

CGC 1090 includes different modes of operation, depending on how fluid is routed through the CGC. The fluid routing is controlled by switch valves 1030, 1034, 1099, 1183 and 1187. In one mode, switch valve 1099 and switch valve 1034 (for detector 1032) are closed, the gases flow towards detector 1028 with switch valve 1030 open. The flow configuration is similar to FIG. 10A when there is no PC/T used or similar to configuration shown in FIG. 10B when a PC/T is used.

In another operating mode of CGC 1090, when the micro switch valve 1099 and switch valve 1034 are open while switch valves 1183 and 1187 are closed, the gases that flow through GC 1008 can be re-circulated back to GC 1002 inlet and pass though GC 1002 again for further gas separation and is then sensed by detector 1032. PC/T 1185 can be included in the flow path between GCs as an option to produce narrower gas spectrum.

Figure 11A:
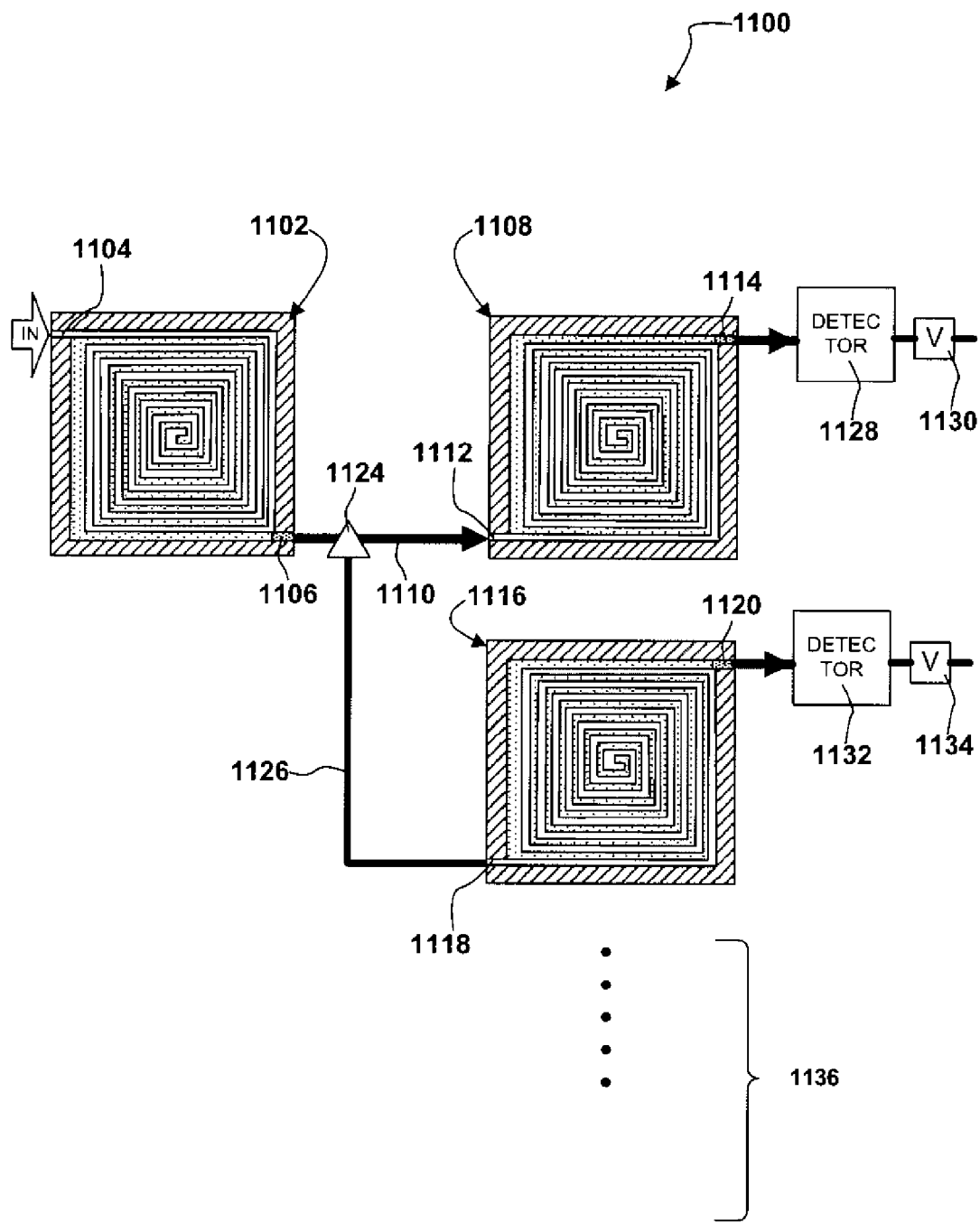
FIG. 11A is a plan-view schematic of an embodiment of a cascaded gas chromatograph.

FIG. 11A illustrates another alternative embodiment of a CGC 1100. CGC 1100 includes GCs 1102, 1108 and 1116. In the illustrated embodiment, GCs 1102 and 1108 are coupled such that outlet 1106 is coupled to inlet 1112 by a fluid connection 1110. Outlet 1114 of GC 1008 is coupled to an inlet of detector 1128, while a switch valve 1130 is coupled to the outlet of detector 1128. An additional fluid connection 1126 is coupled to fluid connection 1110 by a flow splitter or three-way valve 1124. Fluid connection 1126 is also coupled to inlet 1118 of GC 1116, while outlet 1120 of GC 1118 is coupled to an inlet of detector 1132. A switch valve 1130 is coupled to the outlet of detector 1132. Although the embodiment illustrated in the figure has only three GCs, in other embodiments one or more additional GCs, as well as other components such as additional fluid connections, flow splitters, three-way valves detectors and switch valves, can be added to form a cascaded array of GCs, as indicated by dots 1136.

The exact characteristics of each GC in CGC 1100, such as column length, column coatings and operating temperature, will usually depend on operational considerations such as the anticipated uses of CGC 1100, what chemicals the CGC will be used to separate, and so on. In some embodiments, GCs 1102, 1108 and 1116 can have the same characteristics, but in other embodiments GCs 1102, 1108 and 1116 need not have the same characteristics and can have different column lengths, column coatings, operating temperatures, etc. In one embodiment, for example, GC 1002 can be coated with material A, which can be especially selective to polar or non-polar chemicals, and can have its optimum temperature control profile to separate specific chemicals. Meanwhile, GCs 1108 and 1116 can have different column lengths and can be coated with other materials B and C which can separate chemicals that GC 1002 cannot resolve (separate); in other words, GCs 1108 and 1116 are complementary to GC 1002. Since each GC can has its own temperatures control, GCs 1108 and 1116 can be optimized to separate the remaining chemicals of interest that are not resolved (separated) by GC 1002. The separated chemicals can then be detected by detector 1128 at the output of GC 1108 and detector 1132 at the outlet of GC 1116.

Figure 12A:
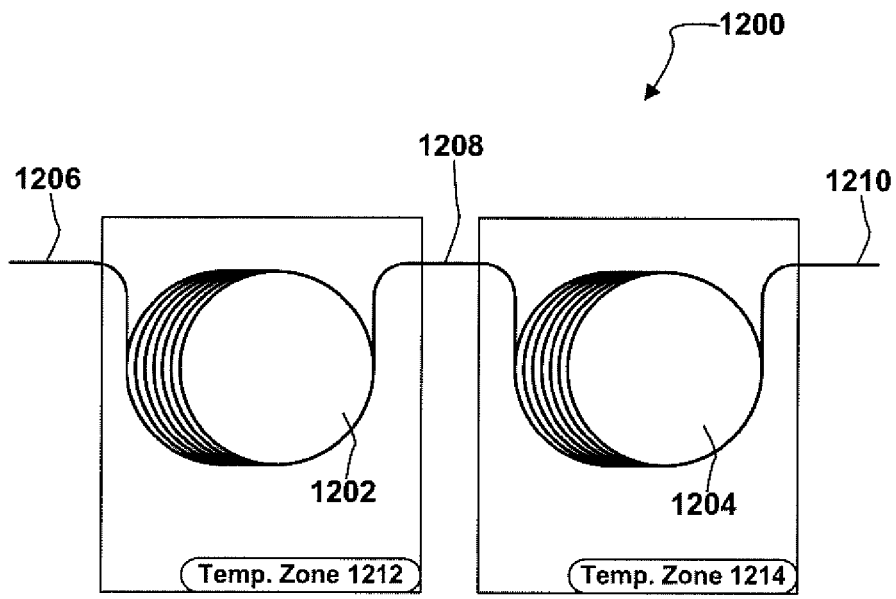
FIGS. 12A-12C are schematic drawings of embodiments of cascaded gas chromatographs using conventional gas chromatographs.
Figure 12B:
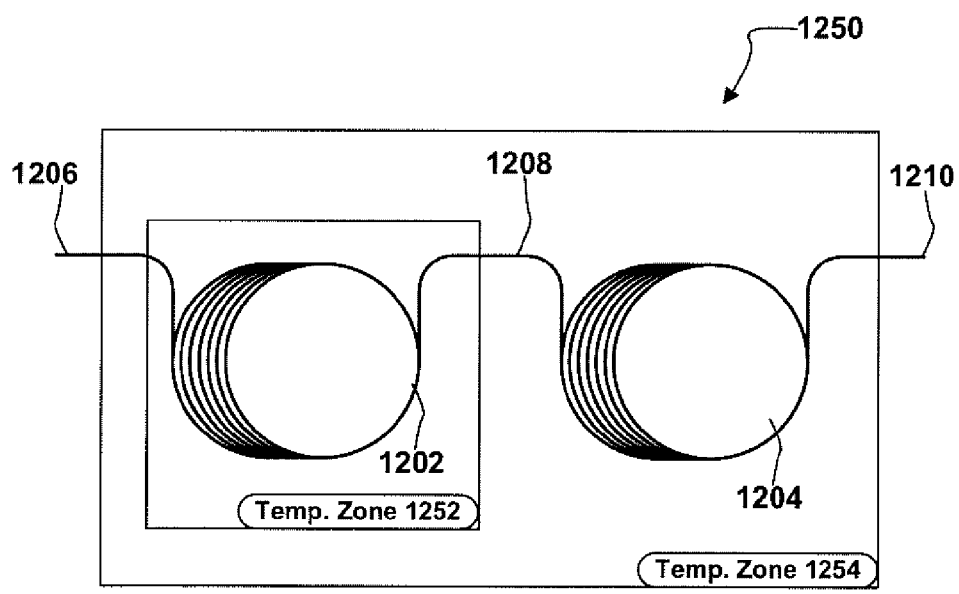
Figure 12C:
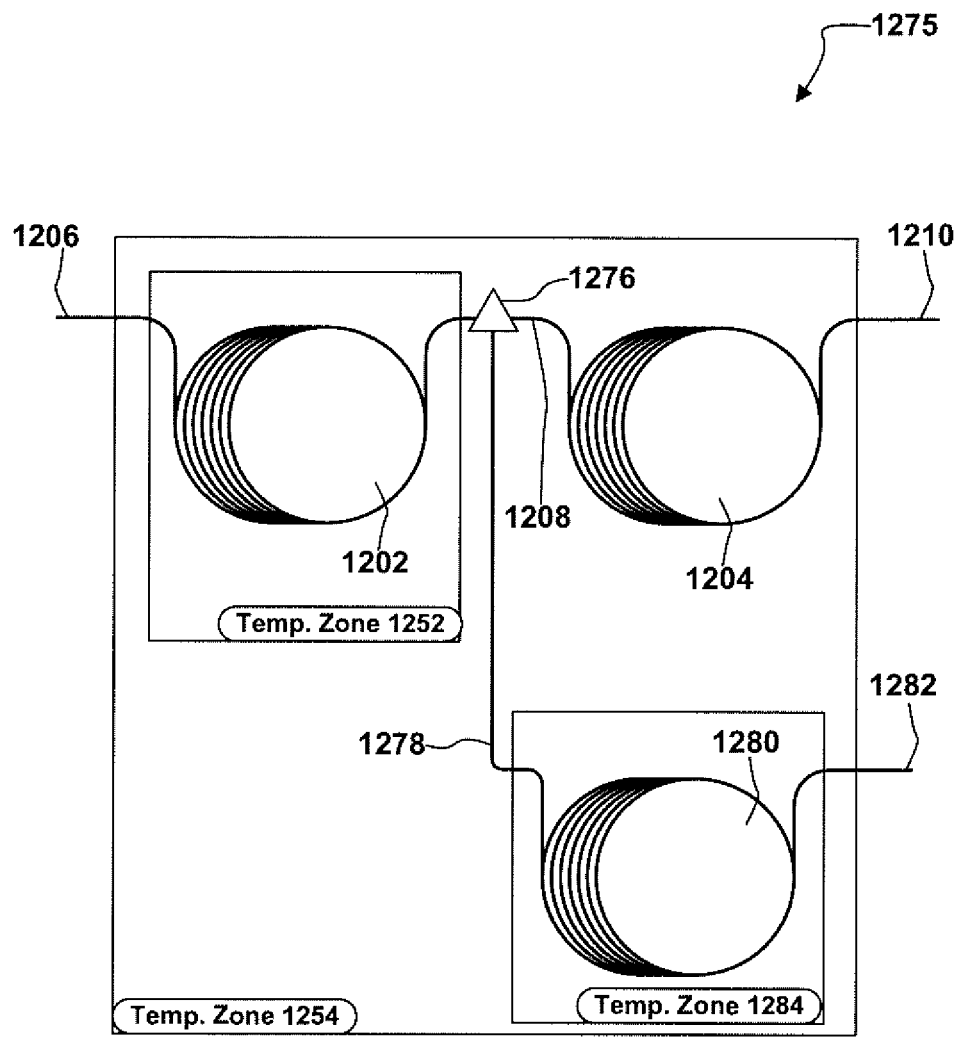

In the illustrated embodiment, GCs 1102, 1108 and 1116 are MEMS gas chromatographs with individual temperature controls, such as those shown in FIG. 3B or 3C, but in other embodiments they can be traditional GCs with individual temperature controls, such as FIG. 3D and the capillary column chromatographs shown in FIGS. 12A-12C. The individual temperature controls allow the temperature of each GC to be controlled independently of the other. In other embodiments GCs 1102, 1108 and 1116 need not be of the same type—that is, CGC 1100 can include both MEMS and non-MEMS chromatographs, can include GCs with different column coatings, different temperature responses, different column configurations, and so forth. In some embodiments all chromatographs can have the same kind of temperature control, but in other embodiments GCs 1102, 1108 and 1116 need not have the same temperature controls; for instance, in the illustrated embodiment with MEMS chromatographs, GCs 1102 and 1108 can have an integrated temperature control as shown in FIG. 3B, while GC 1116 can have an external temperature control, as shown in FIG. 3C.

CGC 1100 includes different modes of operation depending on how fluid is routed through the CGC. In an embodiment in which element 1124 is a flow splitter, the fluid routing is controlled by the operation of switch valves 1130 and 1134. A carrier fluid having one or more chemicals therein enters GC 1102 through inlet 1104 and flows through the GC's column. The GC's temperature control is used to establish and/or maintain the temperature of GC 1102 at the temperature needed for the desired separation of the chemicals from the fluid. The carrier fluid, with any chemicals not resolved (separated) by GC 1102, exits through outlet 1106 into fluid connection 1110.

After exiting GC 1102, a portion of the fluid carried by fluid connection 1110 is directed into GC 1108, and a portion of the fluid is directed into GC 1116 through fluid connection 1126. The portion entering GC 1108 flows through the GC's column and some or all of the unresolved chemicals remaining after GC 1102 are separated. As with GC 1102, the temperature control of GC 1108 is used to establish and/or maintain the temperature needed for the desired separation of the chemicals from the fluid. Outlet 1114 of GC 1108 is coupled to a detector 1128, which can then be used to detect the chemicals separated from the carrier fluid by the two GCs. The portion of fluid entering GC 1116 flows through the GC's column and some or all of the unresolved chemicals remaining after GC 1102 are separated. As with GC 1102, the temperature control of GC 1116 can be used to establish and/or maintain the temperature needed for the desired separation of the chemicals from the fluid. Outlet 1120 of GC 1116 is coupled to detector 1132, which can then be used to detect the chemicals separated from the carrier fluid by the two GCs.

When both switch valves 1130 and 1134 are opened, carrier fluid with chemicals not separated by GC 1102 can be input to GCs 1108 and 1116 for further separation, after which the separated chemicals can be sensed by detectors 1128 and 1132. In an alternative mode of operation where element 1124 is a flow splitter, only one of switch valves 1130 and 1134 can be opened. In such a case, the flow path can be switched between GCs 1108 and 1116 without losing partial gases (lower gases amount to be sensed). In an embodiment in which element 1124 is a three-way valve, the three-way valve can be used to control the flow between GCs 1108 and 1116, and switch valves 1128 and 1132 can be eliminated. By combining the output spectrums from all the detectors, the resulting cascaded micro-GC connection array can produce multi-dimensional gas spectrums, which can significantly boost the gas selectivity and separation power of such system.

Figure 11B:
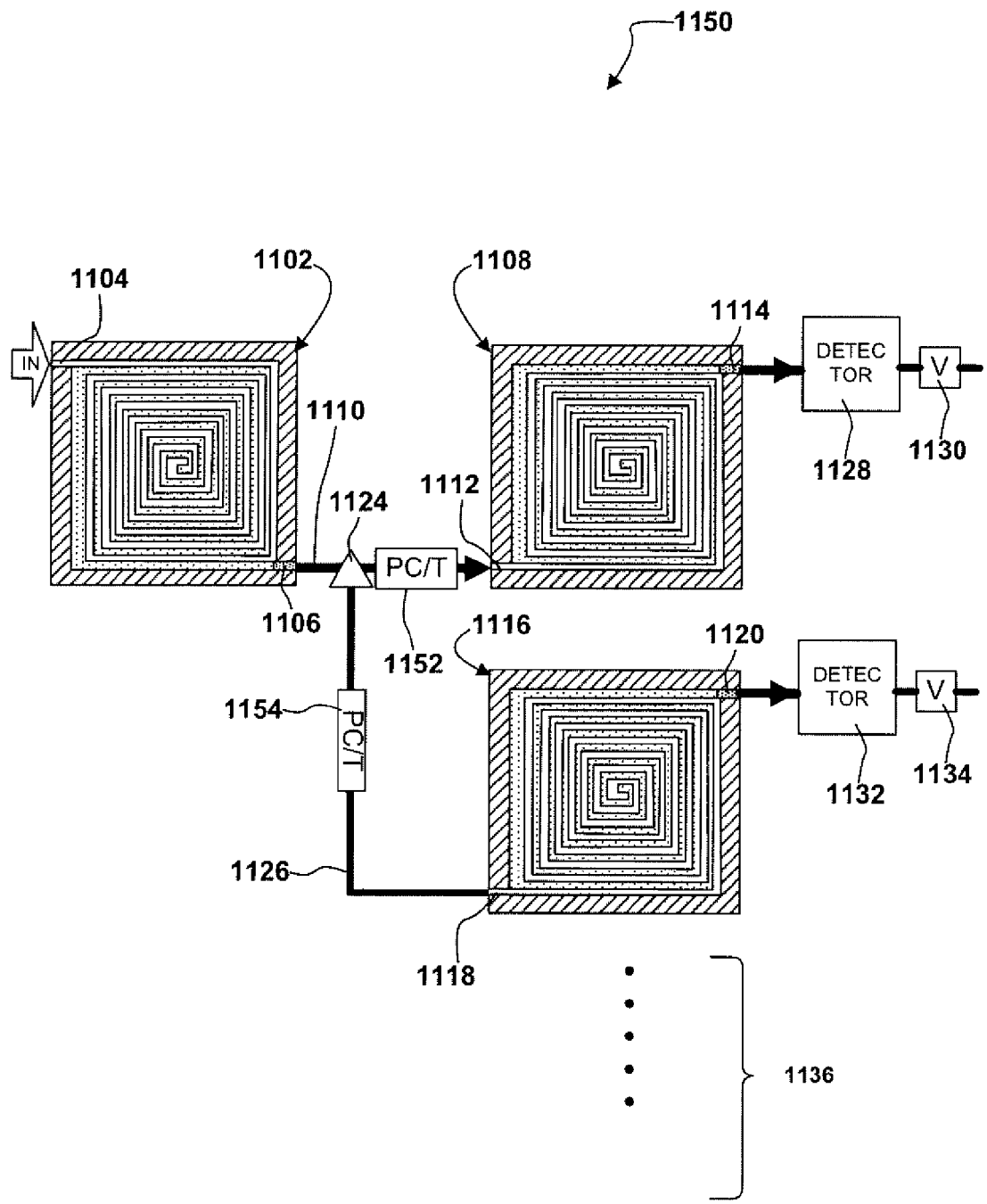
FIG. 11B is a plan-view schematic of an alternative embodiment of a cascaded gas chromatograph.

FIG. 11B illustrates an alternative embodiment of a CGC 1150. CGC 1150 is in most respects similar to CGC 1100. The primary difference between the two is the presence in CGC 1150 of a pre-concentrators and/or traps (PC/T) in fluid connections 1110 and 1126 to periodically trap/release narrow and higher concentration gas spectrums for detector sensing. CGC 1150 operates in a manner similar to CGC 1110, except that PC/Ts 1152 and 1154 are used to periodically trap/release narrow and higher concentration gas spectrums for detector sensing.

Figure 11C:
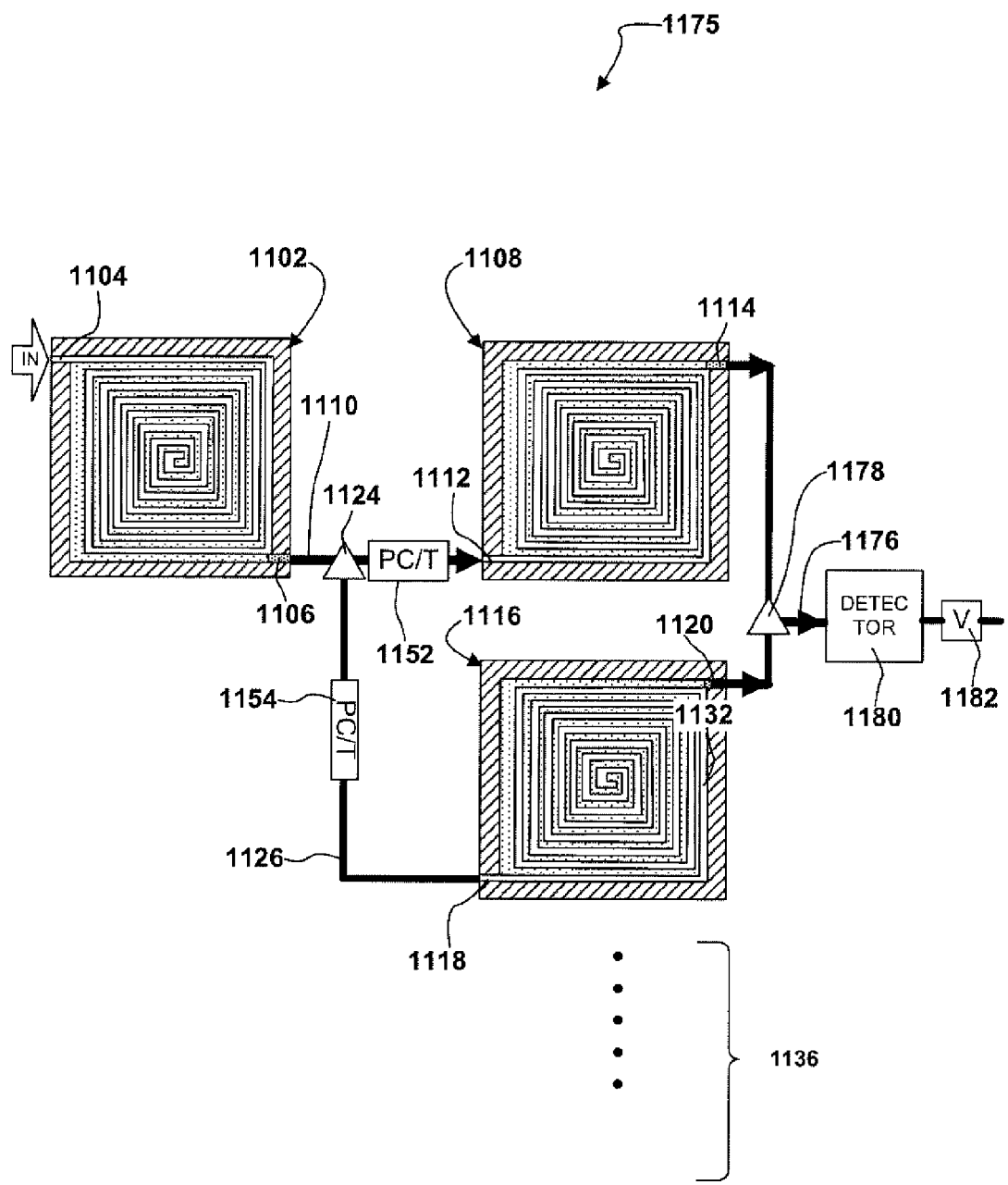
FIG. 11C is a plan-view schematic of another alternative embodiment of a cascaded gas chromatograph.

FIG. 11C illustrates an alternative embodiment of a CGC 1175. CGC 1175 is in most respects similar to CGCs 1100 and 1150. The primary difference in CGC 1175 is that outlet 1114 of GC 1108 and outlet 1120 of GC 1116 are coupled to a common outlet 1176 by element 1178. A common outlet is one that is shared by two or more other individual outlets; in other words, a common outlet is one into which at least two individual other outlets can direct their flow. In one embodiment, element 1178 can be one or more valves, but in other embodiments it can be another element such as one or more flow diverters, or in still other embodiments can be some combination of one or more valves with one or more flow diverters. A detector 1180 and switch valve 1182 can also be coupled to common outlet 1176.

In some embodiments of CGC 1175 the flow from the individual outlets can be directed into the common outlet simultaneously, but in other embodiments the flow from individual outlets into the common outlet need not be simultaneous. In an embodiment of CGC 1175 where element 1178 is a flow splitter, CGC 1175 operates similarly to CGCs 1110 and 1150, except that the flow from both GCs 1108 and 1116 is simultaneously routed into detector 1180. In an embodiment of CGC 1175 where element 1178 includes one or more valves, the valve or valves can be used to switch between the outlet of GC 1108 and the outlet of GC 1116, so that at any given time detector 1180 receives flow from only one of GCs 1108 and 1116. As with CGCs 1100 and 1150, in other embodiments one or more additional GCs, as well as other components such as additional fluid connections, flow splitters, three-way valves detectors and switch valves, can be added to form a cascaded array of GCs, as indicated by dots 1136. In such embodiments, groups of two or more GCs can be coupled to one or more common outlets, so that there need not be a one-to-one correspondence between the number of detectors and the number of GCs.

FIGS. 12A-12C illustrate alternative embodiments of cascaded gas chromatographs (CGCs) using non-MEMS chromatographs, such as capillary column (or capillary channel) chromatographs. FIG. 12A illustrates a cascaded gas chromatograph (CGC) 1200 that includes a first gas chromatograph (GC) 1202 coupled to a second GC 1204. In the illustrated embodiment, GCs 1202 and 1204 are capillary column gas chromatographs coupled in series, such that outlet of GC 1202 is coupled to an inlet of GC 1204 by a fluid connection 1208. Outlet 1210 of GC 1008 can be coupled to another component such as a detector, for example as shown in FIG. 10A.

In the illustrated embodiment, GCs 1202 and 1204 are kept in separate temperature zones, each with its own individual temperature controls: GC 1202 is in temperature zone 1212, while GC 1204 is in temperature zone 1214. Temperature zone 1212 can be controlled independently of temperature zone 1214, so that the temperatures of the GCs can be controlled independently. In one embodiment, temperature zones 1212 and 1214 can be individually controllable ovens or autoclaves, while in other embodiments temperature zones 1212 and 1214 can be individually controllable refrigeration units. In another embodiment, the temperature zones can be individual thermally-insulated temperature substrate or enclosure as shown in FIG. 3D. In other embodiments, temperature zones 1212 and 1214 need not be the same type; for instance, in one embodiment temperature zone 1212 can be an oven while temperature zone 1214 can be a refrigeration unit. In still other embodiments, at least one of temperature zones 1212 and 1214 can be capable of both heating and cooling.

In operation of CGC 1200, a carrier fluid having one or more chemicals therein enters GC 1202 through inlet 1206 and flows through the GC's column. Temperature zone 1212 is used to establish and/or maintain the temperature of GC 1202 at the temperature needed for the desired separation of the chemicals from the fluid. The carrier fluid, with any chemicals not resolved (separated) by GC 1202, exits into fluid connection 1208. Fluid connection 1208 carries the fluid into GC 1204, where the fluid flows through the GC's column and some or all of the unresolved chemicals remaining after GC 1202 are separated. As with GC 1002, temperature zone 1214 is used to establish and/or maintain the temperature needed for the desired separation of chemicals from the fluid in GC 1204. Outlet 1210 of GC 1204 can be coupled to a detector, which can then be used to detect the chemicals separated from the carrier fluid by the two GCs.

FIG. 12B illustrates an alternative embodiment of a CGC 1250. CGC 1250 is in most respects similar to CGC 1200. In CGC 1250, GC 1202 is within temperature zone 1252, while GC 1204 is within temperature zone 1254. The primary difference between CGC 1200 and CGC 1250 is the configuration of the temperature zones: in the illustrated embodiment, temperature zone 1252 is within temperature zone 1254. In one embodiment, temperature zone 1254 can be an oven or autoclave while temperature zone 1252 is a sub-oven within temperature zone 1252, but thermally insulated from temperature zone 1252 and independently controllable from temperature zone 1252. In another embodiment temperature zone 1254 can be a refrigeration unit while temperature zone 1252 is a sub-unit within temperature zone 1252, but thermally insulated from temperature zone 1252 and independently controllable from temperature zone 1252. CGC 1250 operates similarly to GC 1200.

FIG. 12C illustrates an alternative embodiment of a CGC 1275. In the illustrated embodiment, GCs 1202, 1204 and 1280 are capillary column GCs coupled such that outlet of GC 1202 is coupled to inlet of GC 1204 by a fluid connection 1208. An additional fluid connection 1278 is coupled to fluid connection 1208 by a flow splitter or three-way valve 1276. Fluid connection 1278 is also coupled to the inlet of GC 1280. Outlet 1210 of GC 1204 and outlet 1282 of GC 1280 can be coupled to additional components such as detectors.

In the illustrated embodiment, GCs 1202, 1204 and 1280 are kept in separate temperature zones, each with its own independent temperature controls: GC 1202 is in temperature zone 1252, GC 1204 is in temperature zone 1254, and GC 1280 is in temperature zone 1284. In one embodiment, temperature zones 1252, 1254 and 1284 can be individually and independently controllable ovens or autoclaves, while in other embodiments temperature zones 1252, 1254 and 1284 can be independently controllable refrigeration units. In other embodiments, temperature zones 1252, 1254 and 1284 need not be the same type; for instance, in one embodiment temperature zone 1252 could be an oven while temperature zones 1254 and 1284 can be refrigeration units. In another embodiment, temperature zone 1254 can be an oven in which temperature zones 1252 and 1284 can be individual thermally-isolated temperature substrate or enclosure as shown in FIG. 3D. In still other embodiments, at least one of temperature zones 1212 and 1214 can be capable of both heating and cooling. Although the embodiment illustrated in the figure has only three GCs, in other embodiments one or more additional GCs and additional temperature zones, as well as other components such as additional fluid connections, flow splitter, three-way valves, detectors and switch valves, can be added to form a cascaded array of GCs.

CGC 1275 includes different modes of operation depending on how fluid is routed through the CGC. In an embodiment in which element 1276 is a flow splitter, the fluid routing is controlled by the operation of switch valves coupled to outlets 1210 and 1282. When both switch valves are opened, carrier fluid with chemicals not separated by GC 1202 can be input to GCs 1204 and 1280 for further separation, after which the separated chemicals can be sensed by detectors coupled to the outlets. In an alternative mode of operation where element 1276 is a flow splitter, only one of the switch valves can be opened. In such a case, the flow path can be switched between GCs 1204 and 1280 without losing partial gases (lower gases amount to be sensed). In an embodiment in which element 1276 is a three-way valve, the three-way valve can be used to control the flow between GCs 1204 and 1280, and switch valves can be eliminated.

DEVICE APPLICATIONS

Pre-clinical studies on human breath analysis have found that certain volatile organic compounds (VOCs) of exhaled human breath are correlated to certain diseases, such as pneumonia, pulmonary tuberculosis (TB), asthma, lung cancer, liver diseases, kidney diseases, etc. The correlations are especially evidential for lung-related diseases. Current analytical systems still rely on large and expensive laboratory instruments, such as gas chromatography (GC) and mass spectrometry (MS). Mass spectrometers in particular are impossible to miniaturize, making widespread use of these diagnostic instruments impossible.

The embodiments of MEMS-based gas analysis sensors discussed above provide a solution to this problem, and in particular could be used advantageously to diagnose and monitor various diseases such as asthma, lung cancer, lung-related diseases, and other non-lung diseases such as kidney and liver diseases, and etc.

Asthma

Asthma is a chronic disease; therefore, regularly monitoring patient's status is helpful to doctor on tracking patient's healing progresses. Therefore, the new idea of handheld diagnostics would make the breath analysis possible done at home or anywhere. In current diagnostics the basic measurement is peak flow rate and the following diagnostic criteria are used by the British Thoracic Society, but the peak flow rate is a physical quantity measurement. Breath analysis could provide specific root causes of the bronchi contraction by measuring the VOCs from patient's breath. Embodiments of the MEMS-based gas analysis systems could be used to monitor the efficacy of the medication. Furthermore, the medication therapy can be tailored to individual patient through this active monitoring by using this home-based device.

Tuberculosis

One third of the world's current population has been infected by TB. And 75% of the cases are pulmonary TB. The infected rate in the developing countries is much higher than developed countries. Therefore, there are urgent needs of developing affordable diagnostic devices for developing countries. Embodiments of the MEMS-based gas analysis system would provide a cost-effective solution. Tuberculosis is caused by Mycobacterium. Current diagnostic is time consuming and difficult since culturing the slow growing Mycobacterium takes about 6 weeks. Therefore, a complete medical evaluation, including chest X-ray, Tuberculosis radiology, tuberculin skin test, microbiological smears and cultures, is used to get more accurate assessment. Therefore, the rapid diagnostic is very valuable and our breath analysis approach could achieve such needs.

Lung Cancer

With early detection and treatment, the 5-year survival rate for lung cancer improves dramatically. Current diagnostic methods, such as chest X-ray and CT (computed tomography) scan, are difficult to detect early stage lung cancer. Breath analysis using embodiments of the MEMS-based gas analysis system could diagnose the early stage lung cancer.

Classification of Lung-Related Diseases with Similar Symptoms

Breath analysis on exhaled VOCs is viable method to identify patient's lung-related diseases, which has similar symptoms. For example, embodiments of the MEMS-based gas analysis system can provide the tested data to medical doctors to classify which disease between cool, lung-cancer, or pneumonia the patient would have. Breath analysis would be the first screening test because of its simplicity before going for more tedious diagnostic measurements.

The above description of illustrated embodiments of the invention, including what is described in the abstract, is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize. These modifications can be made to the invention in light of the above detailed description.

The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

The invention claimed is:

1. A gas analysis system comprising:
a substrate;
a cascaded gas chromatograph having a fluid inlet and one or more fluid outlets and being mounted to the substrate, the cascaded gas chromatograph comprising:
   a first gas chromatograph including a separation column formed in or on a first substrate and a first thermoelectric cooler thermally coupled to the first substrate, wherein the first thermoelectric cooler can both heat and cool the separation column of the first gas chromatograph,
   a second gas chromatograph including a separation column formed in or on a second substrate and a second thermoelectric cooler thermally coupled to the second substrate, wherein the second thermoelectric cooler can both heat and cool the separation column of the second gas chromatograph, and wherein the second thermoelectric cooler is independent of the first thermoelectric cooler,
   a fluid connection coupled between an outlet of the first gas chromatograph and an inlet of the second gas chromatograph, and
   a valve, a flow splitter, a pre-concentrator, or a trap coupled in the fluid connection between the outlet of the first gas chromatograph and the inlet of the second gas chromatograph;
one or more detector arrays having a fluid inlet and a fluid outlet and being mounted to the substrate, wherein the fluid inlet of each of the one or more detector arrays is fluidly coupled to a corresponding one of the one or more fluid outlets of the cascaded gas chromatograph;
a control circuit coupled to the cascaded gas chromatograph and to the detector array, wherein the control circuit can communicate with the first and second gas chromatographs and with the one or more detector arrays;
a readout circuit coupled to the one or more detector arrays and to the control circuit, wherein the readout circuit can communicate with the control circuit and the one or more detector arrays;
a pre-concentrator having a fluid inlet and a fluid outlet, wherein the pre-concentrator is mounted on the substrate and coupled to the control circuit, and wherein the fluid outlet of the pre-concentrator is coupled to the fluid inlet of the cascaded gas chromatograph;
a filter and valve unit having a fluid inlet and a fluid outlet, wherein the filter and valve unit is mounted to the substrate and coupled to the control circuit, and wherein the fluid outlet of the filter and valve unit is coupled to the fluid inlet of the pre-concentrator;
one or more pumps having a fluid inlet and a fluid outlet, wherein each pump is mounted on the substrate and coupled to the control circuit, and wherein the fluid inlet of each pump is coupled to the fluid outlet of a corresponding detector array; and
a shroud covering the filter and valve unit, the pre-concentrator, the cascaded gas chromatograph, the one or more detector arrays and the pump.

2. The gas analysis system of claim 1, further comprising a recirculating fluid connection coupled between an inlet of the first gas chromatograph and an outlet of the second gas chromatograph.

3. The gas analysis system of claim 1 wherein the shroud provides the fluid connection among the filter and valve unit, the pre-concentrator, the cascaded gas chromatograph, the one or more detector arrays and the pump.

4. The gas analysis system of claim 1, further comprising a communication interface coupled to the readout circuit to allow the gas analysis system to communicate with an external device.

5. The gas analysis system of claim 1, further comprising one or more additional gas chromatographs, each including an independent thermoelectric cooler, wherein the one or more additional gas chromatographs are fluidly coupled to the fluid connection between the first gas chromatograph and the second gas chromatograph.

6. The gas analysis system of claim 5 wherein an outlet of the second gas chromatograph and an outlet of at least one of the one or more additional gas chromatographs are coupled to a common outlet.

7. The gas analysis system of claim 1 wherein the readout circuit includes thereon an analysis circuit and associated logic to analyze an output signals received from the one or more detector arrays.

8. The gas analysis system of claim 7, further comprising an indicator coupled to an output of the analysis circuit to indicate to a user a result of the analysis.

\* \* \* \* \*